(12) United States Patent
Gauthier

(10) Patent No.: US 8,918,177 B2
(45) Date of Patent: Dec. 23, 2014

(54) METHOD AND SYSTEM TO FACILITATE NEUROSTIMULATOR PROGRAMMING BASED ON PRE-EXISTING THERAPY PROFILES

(75) Inventor: Marc Gauthier, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 195 days.

(21) Appl. No.: 13/552,477

(22) Filed: Jul. 18, 2012

(65) Prior Publication Data

US 2013/0023950 A1    Jan. 24, 2013

Related U.S. Application Data

(60) Provisional application No. 61/509,249, filed on Jul. 19, 2011.

(51) Int. Cl.
*A61N 1/05* (2006.01)
*A61N 1/372* (2006.01)

(52) U.S. Cl.
CPC ........ *A61N 1/37247* (2013.01); *A61N 1/37282* (2013.01)
USPC .......................................................... 607/46

(58) Field of Classification Search
USPC .......................................................... 607/46
See application file for complete search history.

(56) References Cited

U.S. PATENT DOCUMENTS

2010/0010566 A1* 1/2010 Thacker et al. .................. 607/46
2010/0121409 A1* 5/2010 Kothandaraman et al. ..... 607/46
2010/0141676 A1   6/2010 Daignault, Jr.
2011/0098778 A1   4/2011 Thimineur et al.
2011/0282414 A1* 11/2011 Kothandaraman et al. ..... 607/59

OTHER PUBLICATIONS

The British Pain Society's "Spinal Cord Stimulation for the Management of Pain: Recommendations for Best Clinical Practice", © The British Pain Society 2009, ISBN: 0-9546703-7-X; pp. 1-56.
David Abejon, MD et al.; "Peripheral Nerve Stimulation or Is It Peripheral Subcutaneous Field Stimulation; What is in a Moniker?"; Jan. 13, 2009; Http://onlinelibrary.wiley.com/doi/10.1111/j.1525-1403.2009.00192.x/full ; 4 pgs.
Tracy Cameron, Ph.D; Safety and Efficacy of Spinal Cord Stimulation for the Treatment of Chronic Pain; a 20-year Literature Review; J. Neurosurg (Spine 30) 100:254-267, 2004.

(Continued)

*Primary Examiner* — Christopher D Koharski
*Assistant Examiner* — Jeremiah Kimball

(57) ABSTRACT

A method and system are provided to assist in programming of a neurostimulator based on a collection of pre-existing therapy profiles. The method and system access a collection of pre-existing therapy profiles derived from prior actual patients or patient models. The pre-existing therapy profiles include stimulation programs mapped to pre-existing patient profiles. The pre-existing patient profiles have at least one of i) prior lead attribute, ii) prior pain maps, and iii) prior stimulation maps for prior patients or models of patients. The method and system further compare the new patient profile with at least a portion of the collection of pre-existing patient profiles to generate profile matching scores indicating an amount of similarity between the pre-existing patient and the new therapy profile.

22 Claims, 13 Drawing Sheets

(56) References Cited

OTHER PUBLICATIONS

Department of Neurological Surgery; "Center for Image-Guided Neurosurgery Deep Brain Stimulation"; University of Pittsburgh, Department of Neurosurgery; http://www.neruosurgery.pitt.edu/imageguided/movement/stimulation.html; 3 pgs.

KL Reed et al.; "Combined Occipital and Supraorbital neurostimulation for the Treatment of Chronic Migraine Headaches: Initial Experience"; Cephalalgia, International Headache Society; CEP.sagepub.com; Published online Feb. 15, 2010; 30(3) 260-271.

Samer N. Narouze, MD et al.; "Supraorbital Nerve Electric Stimulation for the Treatment of Intractable Chronic Cluster Headache: A Case Report"; pain Management Department, The Cleveland clinic Foundation, Cleveland OH, USA, Apr. 30, 2007: 1100-1102.

Richard M. Paicius, MD et al.; "Peripheral Nerve Field Stimulation in Chronic Abdominal Pain"; Pain Physician; 2006; 9:261-266, ISSN 1533-3159.

Bengt Linderoth et al.: "Chapter 37: Spinal Cord and Brain Stimulation"; pp. 1-20.

* cited by examiner

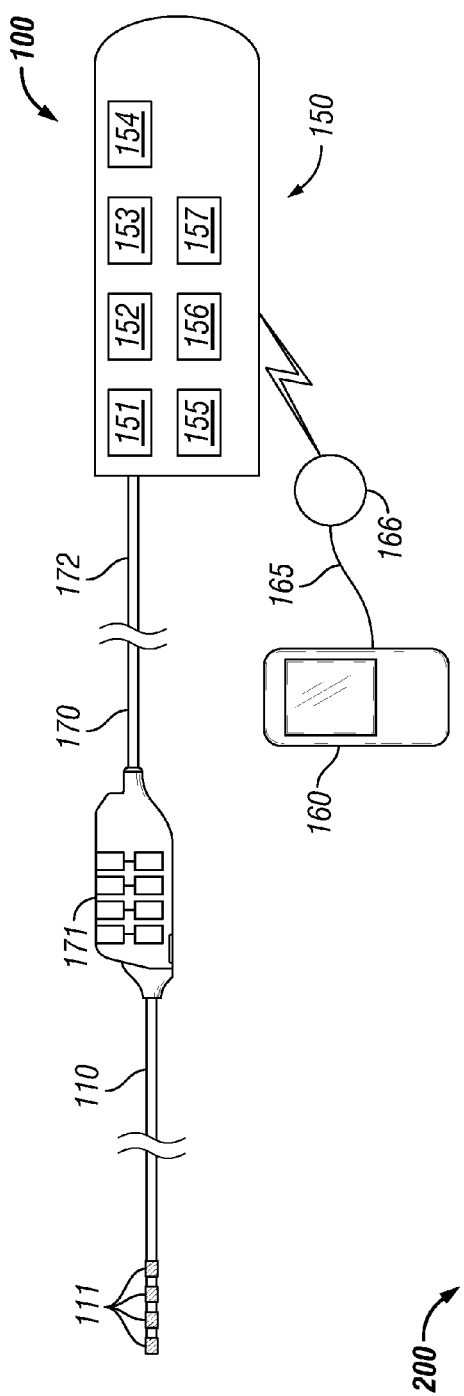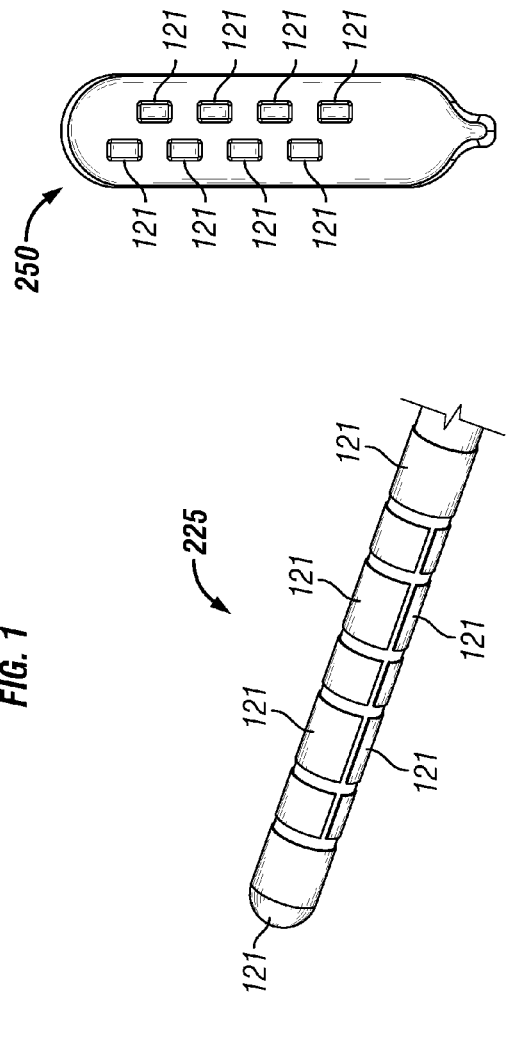
FIG. 1
FIG. 2A
FIG. 2B
FIG. 2C

904 → Lead Type

|   | 1 | 2 | 3 | 4 | 5 | 6 | 7 | 8 | 9 | 10 |
|---|---|---|---|---|---|---|---|---|---|----|
| 1 | 10 | 9 | 7 | 3 | 2 | 5 | 3 | 7 | 1 | 8 |
| 2 | 9 | 10 | 8 | 7 | 7 | 3 | 9 | 2 | 1 | 6 |
| 3 | 7 | 9 | 10 | 9 | 7 | 9 | 6 | 8 | 7 | 9 |
| 4 | 3 | 7 | 9 | 10 | 9 | 7 | 2 | 1 | 4 | 3 |
| 5 | 2 | 7 | 7 | 9 | 10 | 9 | 7 | 6 | 3 | 1 |
| 6 | 5 | 3 | 9 | 7 | 9 | 10 | 9 | 7 | 7 | 4 |
| 7 | 3 | 9 | 6 | 2 | 7 | 9 | 10 | 9 | 7 | 5 |
| 8 | 7 | 2 | 8 | 1 | 6 | 7 | 9 | 10 | 9 | 7 |
| 9 | 1 | 1 | 7 | 4 | 3 | 7 | 7 | 9 | 10 | 9 |
| 10 | 8 | 6 | 9 | 3 | 1 | 4 | 5 | 7 | 9 | 10 |

902 → Lead Type (row axis)

FIG. 9

METHOD AND SYSTEM TO FACILITATE NEUROSTIMULATOR PROGRAMMING BASED ON PRE-EXISTING THERAPY PROFILES

CROSS-REFERENCE TO RELATED APPLICATIONS

This application claims the benefit of U.S. Provisional Application No. 61/509,249, filed Jul. 19, 2011, which is incorporated herein by reference.

BACKGROUND OF THE INVENTION

Embodiments of the present invention generally relate to programming of neurostimulators and more particularly to methods and systems to assist in programming neurostimulators based on a collection of pre-existing therapy profiles.

Neurostimulation systems are devices that generate electrical pulses and deliver the pulses to nerve tissue to treat a variety of disorders. Spinal cord stimulation (SCS) is the most common type of neurostimulation. In SCS, electrical pulses are delivered to nerve tissue in the spine typically for the purpose of chronic pain control. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

SCS systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals, which are also electrically coupled to the wire conductors that are adapted to receive electrical pulses. The distal end of a respective stimulation lead is implanted within the epidural space to deliver the electrical pulses to the appropriate nerve tissue within the spinal cord that corresponds to the dermatome(s) in which the patient experiences chronic pain. The stimulation leads are then tunneled to another location within the patient's body to be electrically connected with a pulse generator or, alternatively, to an "extension."

The pulse generator is typically implanted within a subcutaneous pocket created during the implantation procedure. In SCS, the subcutaneous pocket is typically disposed in a lower back region, although subclavicular implantations and lower abdominal implantations are commonly employed for other types of neuromodulation therapies. The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator.

Existing programmer devices for neurostimulators do not provide any programming assistance or recommendations to a clinician regarding stimulation programs that may be effective for a patient exhibiting certain characteristics. Instead, existing programmer devices act as dumb interfaces forcing the clinician to rely on his or her training and experience in determine the stimulation parameters that may be effective. This process is time consuming and success of the outcome may vary across patients, sessions, and clinicians. Training of new clinicians is expensive and time-consuming because existing neurostimulator and programming devices requires a solid understanding of anatomical, physiological, and electrical principles. Existing devices do not leverage the collective programming knowledge of existing clinicians to promote good programming practices and avoid programs that tend to be ineffective.

For purposes of spinal cord stimulation (SCS), or the controlled application of specific electrical energy to certain spinal nervous tissue to manage the transmission of specialized pain signals through such tissue, systems have been proposed that map "pain" data to predetermined regions of the patient. Pain maps have been drawn on a graphical image of a human figure. However, pain maps for individual patients are not readily accessible to clinicians who are trying to determine what stimulation program would be effective with another patient.

Further, current technology does not afford a mechanism to utilize pain maps from multiple patients in connection with determining stimulation programs for new patients.

Another negative characteristic of current technology is the limited amount (and quality) of pain-related information recorded and considered. In particular, indicating pain relative to a human representation simply provides relative location information. Any pain characteristics are limited to an intensity value, which is entered through a textual-based, numeric input mechanism.

Consequently, a need exists for a system that enables an object, whether predisposed to regional division or not, to be mapped into a plurality of regions, each region being capable of capturing region-specific and/or object-specific data. A need exists for a system in which users can consistently and reliably enter information attributable to any given region. A need exists for a system that would enable data for any given lead attribute or pain map to be compared, universally modified, and/or otherwise manipulated among a plurality of programming devices.

SUMMARY OF THE INVENTION

In accordance with an embodiment, methods and systems are provided that expedite programming of neurostimulators and increase the probability of achieving an effective therapy profile by leveraging prior programming experience which is recorded as a collection of pre-existing therapy profiles and maintained in a shared database.

In accordance with an embodiment, methods and systems are provided that utilize a shared database of patient profiles and associated stimulation programs. The database is maintained by an automated programming assistant (APA) that receives patient and programming information including patient profiles that may include pain maps, lead placement, lead type, lead orientation, electrode configuration, stimulation parameters and the like. The APA receives the patient profiles and programming information from programming devices that are deployed and in use. Upon request, these programming devices receive, from the automated programming assistant, recommended stimulation programs that match a new patient profile. The automated programming assistant uses various matching algorithms to match therapy profiles for patients with similar pain maps and lead placement and account for anatomical variations across the patient population.

In accordance with various embodiments, methods and systems are provided that afford various benefits over prior programming devices. For example, these benefits include, but are not limited to, the following: a) recording a collection of patient profiles, that are associated with corresponding stimulation programs, into a shared database, b) recording a collection of effective stimulation programs into a shared database, c) affording a process to correlate similar/matching patient profiles, d) providing an automated recommendation of applicable programs based on correlated patient profile, and e) decoupling of stimulation programs from variations between different patient's anatomies.

In accordance with an embodiment, a method is provided to assist in programming of a neurostimulator based on a collection of pre-existing therapy profiles. The method comprises obtaining a new patient profile for a new patient receiving a neurostimulator and displays a virtual lead and a graphical representation of an anatomy of interest. The method permits a clinician to position and/or orient the virtual lead on the anatomy of interest at a corresponding placement or orientation representative of a position or an orientation at which an actual lead was implanted in the new patient. The new therapy profile includes at least one of i) a planned lead attribute, ii) a new pain map, and iii) a new stimulation map for the new patient receiving the neurostimulator. The planned and prior lead attributes include at least one of lead type, lead placement and lead orientation. The method further provides the obtaining to include recording, as the planned lead attribute, at least one of a new lead type, new lead placement and new lead orientation after implantation of the lead relative to anatomical structure in a manner that is independent of variations in patient dimensions.

The method further accesses a collection of pre-existing therapy profiles derived from prior actual patients or patient models. The accessing includes querying at least one database that stores the collection of pre-existing therapy profiles. The pre-existing therapy profiles include stimulation programs mapped to pre-existing patient profiles. The pre-existing patient profiles have at least one of i) prior lead attribute, ii) prior pain maps, and iii) prior stimulation maps for prior patients or models of patients.

The method compares the new patient profile with at least a portion of the collection of pre-existing patient profiles to generate profile matching scores which indicates an amount of similarity between the pre-existing patient and the new therapy profile. The method further produces a list of candidate therapy profiles that include at least one potential stimulation program that is mapped to at least one pre-existing patient profile having a profile matching score that satisfies a match threshold. The method further comprises the comparing to include utilizing a matching function to generate similarity ratings between the planned and prior lead attributes of the new patient profile and the pre-existing patient profiles, and utilizing the similarity ratings to generate the profile matching scores. The matching function forms the similarity ratings between at least one of i) a planned lead placement and prior lead placements and ii) a planned lead orientation and prior lead orientations. The method additionally comprises the comparing to include utilizing a matching function to form pain overlap scores between the new pain map and the prior pain maps, and utilizing the pain overlap scores to generate the profile matching scores.

In accordance with an embodiment, a system is provided to assist in programming a neurostimulator based on a collection of pre-existing therapy profiles. The system provides an input device to obtain a new patient profile for a new patient receiving a neurostimulator. The new therapy profile includes at least one of i) a planned lead attribute, ii) a new pain map, and iii) a new stimulation map for the new patient receiving the neurostimulator. The system further provides a storage storing a collection of pre-existing therapy profiles derived from prior actual patients or patient models. The pre-existing therapy profiles include stimulation programs mapped to pre-existing patient profiles, the pre-existing patient profiles having at least one of i) prior lead attributes, ii) prior pain maps, and iii) prior stimulation maps for prior patients or models of patients.

In accordance with an embodiment, the system provides a comparator module to compare the new patient profile with at least a portion of the collection of pre-existing patient profiles to generate profile matching scores indicating an amount of similarity between the pre-existing patient profiles and the new therapy profile. The system further provides a candidate module to produce a list of candidate therapy profiles that include at least one potential stimulation program that is mapped to at least one pre-existing patient profile having a profile matching score that satisfied a match threshold.

BRIEF DESCRIPTION OF THE DRAWINGS

FIG. 1 depicts a stimulation system formed according to a representative embodiment.

FIGS. 2A-2C respectively depict stimulation portions for inclusion at the distal end of a lead according to some representative embodiments.

FIG. 9 illustrates an exemplary type matching table utilized to obtain lead type similarity ratings.

DETAILED DESCRIPTION

Figure 3A:
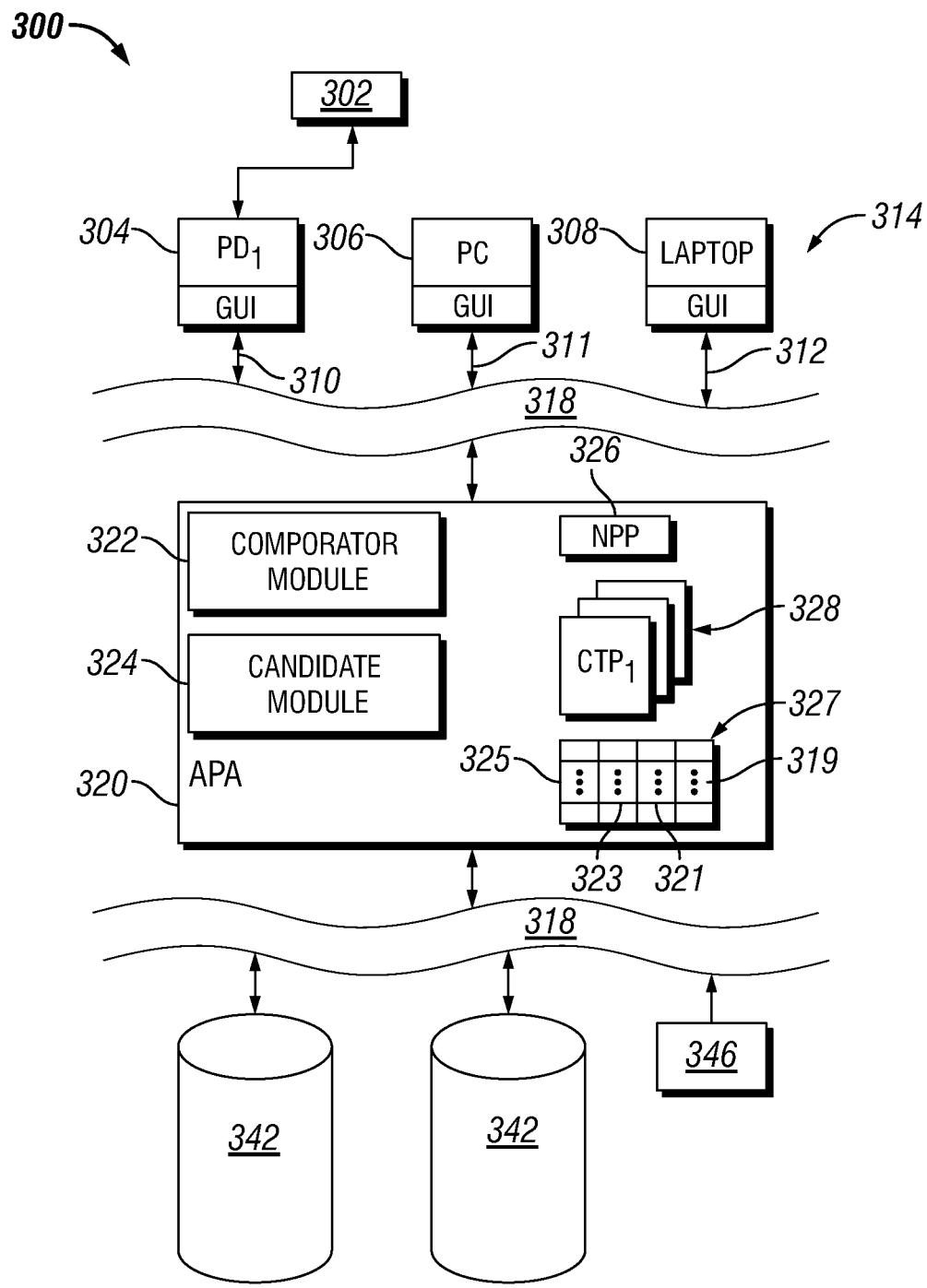
FIG. 3A illustrates a block diagram of an exemplary system to collect therapy profiles and to assist in programming a neurostimulator based on a collection of pre-existing therapy profiles in accordance with an embodiment.

FIG. 1 depicts stimulation system 100 that generates electrical pulses for application to tissue of a patient according to one embodiment. For example, system 100 may be adapted to stimulate spinal cord tissue, peripheral nerve tissue, deep brain tissue, cortical tissue, cardiac tissue, digestive tissue, pelvic floor tissue, or any other suitable tissue within a patient's body.

System 100 includes implantable pulse generator 150 that is adapted to generate electrical pulses for application to tissue of a patient. Implantable pulse generator 150 typically comprises a metallic housing that encloses controller 151, pulse generating circuitry 152, charging coil 153, battery 154, far-field and/or near field communication circuitry 155, battery charging circuitry 156, switching circuitry 157, etc. of the device. Controller 151 typically includes a microcontroller or other suitable processor for controlling the various other components of the device. Software code is typically stored in memory of the pulse generator 150 for execution by the microcontroller or processor to control the various components of the device.

Pulse generator 150 may comprise a separate or an attached extension component 170. If extension component 170 is a separate component, extension component 170 may connect with the "header" portion of pulse generator 150 as is known in the art. If extension component 170 is integrated with pulse generator 150, internal electrical connections may be made through respective conductive components. Within pulse generator 150, electrical pulses are generated by pulse generating circuitry 152 and are provided to switching circuitry 157. The switching circuit connects to outputs of pulse generator 150. Electrical connectors (e.g., "Bal-Seal" connectors) within connector portion 171 of extension component 170 or within the IPG header may be employed to conduct the stimulation pulses. The terminals of one or more stimulation leads 110 are inserted within connector portion 171 or within the IPG header for electrical connection with respective connectors. Thereby, the pulses originating from pulse generator 150 are provided to stimulation lead 110. The pulses are then conducted through the conductors of lead 110 and applied to tissue of a patient via electrodes 111. Any suitable known or later developed design may be employed for connector portion 171.

For implementation of the components within pulse generator 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 20060170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within pulse generator 150. Different pulses on different electrodes may be generated using a single set of pulse generating circuitry using consecutively generated pulses according to a "multi-stimset program". Complex pulse parameters may be employed such as those described in U.S. Pat. No. 7,228,179, entitled "Method and apparatus for providing complex tissue stimulation patterns," and International Patent Publication Number WO/2001/093953 A1, entitled "NEUROMODULATION THERAPY SYSTEM," which are incorporated herein by reference. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may comprise a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number of electrodes 111, terminals, and internal conductors.

FIGS. 2A-2C respectively depict stimulation portions 200, 225, and 250 for inclusion at the distal end of lead 110. Stimulation portion 200 depicts a conventional stimulation portion of a "percutaneous" lead with multiple ring electrodes 121. Stimulation portion 225 depicts a stimulation portion including several "segmented electrodes"121. The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another. Example fabrication processes are disclosed in U.S. Patent Publication No. 2011/0072657, entitled, "METHOD OF FABRICATING STIMULATION LEAD FOR APPLYING ELECTRICAL STIMULATION TO TISSUE OF A PATIENT," which is incorporated herein by reference. Stimulation portion 250 includes multiple planar electrodes on a paddle structure.

Although not required for all embodiments, the lead bodies of lead(s) 110 and extension component 170 may be fabricated to flex and elongate in response to patient movements upon implantation within the patient. By fabricating lead bodies according to some embodiments, a lead body or a portion thereof is capable of elastic elongation under relatively low stretching forces. Also, after removal of the stretching force, the lead body is capable of resuming its original length and profile. For example, the lead body may stretch 10%, 20%, 25%, 35%, or even up or above to 50% at forces of about 0.5, 1.0, and/or 2.0 pounds of stretching force.

The ability to elongate at relatively low forces may present one or more advantages for implantation in a patient. For example, as a patient changes posture (e.g., "bends" the patient's back), the distance from the implanted pulse generator to the stimulation target location changes. The lead body may elongate in response to such changes in posture without damaging the conductors of the lead body or disconnecting from pulse generator. Also, deep brain stimulation implants, cortical stimulation implants, and occipital subcutaneous stimulation implants usually involve tunneling of the lead body through tissue of the patient's neck to a location below the clavicle. Movement of the patient's neck subjects a stimulation lead to significant flexing and twisting which may damage the conductors of the lead body. Due to the ability to elastically elongate responsive to movement of the patient's neck, certain lead bodies according to some embodiments are better adapted for such implants than some other known lead body designs. Fabrication techniques and material characteristics for "body compliant" leads are disclosed in greater detail in U.S. Provisional Patent Application Ser. No. 60/788,518, entitled "Lead Body Manufacturing," filed Mar. 31, 2006, which is incorporated herein by reference.

Controller device 160 may be implemented to recharge battery 153 of pulse generator 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller 160 generates an AC-signal to drive current through coil 166 of wand 165. Assuming that primary coil 166 and secondary coil are suitably positioned relative to each other, the secondary coil is disposed within the field generated by the current driven through primary coil 166. Current is then induced in secondary coil. The current induced in the coil of the implantable pulse generator is rectified and regulated to recharge battery 154 by charging circuitry 156. Charging circuitry 156 may also communicate status messages to controller 160 during charging operations using pulse-loading or any other suitable technique. For example, controller 160 may communicate the coupling status, charging status, charge completion status, etc.

External controller device 160 is also a device that permits the operations of pulse generator 150 to be controlled by user after pulse generator 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 150.

Controller device 160 preferably provides one or more user interfaces to allow the user to operate pulse generator 150. The user interfaces may permit the user to move electrical stimulation along and/or across one or more stimulation leads using different electrode combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is incorporated herein by reference. Also, controller device 160 may permit operation of IPG 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. IPG 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

FIG. 3A illustrates a block diagram of an exemplary system to collect patient profiles and stimulation programs and to assist in programming a neurostimulator based on a collection of pre-existing therapy profiles in accordance with an embodiment. The system 300 illustrates a neurostimulator 302 that wirelessly communicates with a programming device 304. The system 300 illustrates various exemplary types of input devices 314. By way of example, the input devices 314 may represent a programming device 304, a personal computer 306, a laptop computer 308 and the like. The input devices 314 are used to permit a clinician to obtain and enter a new patient profile for a patient that has or is about to receive the neurostimulator 302. The new patient profile includes various types of information, such as lead attributes. Lead attributes may include one or more of a planned lead type, a planned lead placement, a planned lead orientation, electrode configurations and the like that is intended to be used or has already been implemented. The new patient profile may also include a pain map representative of the locations and intensity of pain experienced by the patient. The patient profile may also include a stimulation map representative of locations and the nature of stimulation felt by the patient when a programmed therapy is delivered. The patient profile may also include dermatome locations for the patient. Examples are described below for methods and structures that may be utilized by a clinician to enter new patient profiles.

The system 300 includes a large number of input devices 314 distributed over a wide geographic area, such as a hospital network, a device type network, a region of the U.S., the entire U.S., North America, Europe, Asia, the world and the like. Input devices 314 throughout the region supported by the network are used to create and upload patient profiles as new patients receive neurostimulators. For example, a clinician uses a programming device 304 to enter a stimulation program, as well as patient profile information (e.g., lead attributes, pain maps, stimulation maps).

The patient profile and stimulation program is conveyed from the input device (304-308) over a network link 310-312 to an automated programming assistant 320 (APA). The communications link between the input devices 314 and the APA 320 may include a private network, the internet, a wide area network, a local area network and the like. The APA 320 stores the patient profile and stimulation program together as a therapy profile in the storage 342. The APA 320 continuously collects and stores therapy profiles based on inputs from a wide geographic area.

The programmable device 304 communicates with the neurostimulator 302 to program various device settings such as the electrode configuration, electrical parameters, pulse pattern (e.g., pulse width, pulse frequency, pulse amplitude), pulse characteristics, pulse timing and other stimulation parameters. The programming device 304 may automatically convey all of the programming information to the APA 320. In addition, the programming device 304 may be used by a clinician to enter the stimulation and pain maps, as well as other types of patient profile information which are all routed to the APA. Optionally, the PC 306 or laptop 308 or another type of input device 304 may be used to enter all or a portion of the patient profile information and stimulation profile. For example, one type of input device may be used to enter the planned lead type and planned lead placement, while another type of input device 314 may be used to enter a pain map and/or a stimulation and/or dermatome locations associated with a patient.

The APA 320 communicates with one or more storage 342, to record therapy profiles and to access pre-existing therapy profiles (PETP). The storages 342 may be maintained in a central location or distributed across multiple locations. A copy of the information in the storages 342 may reside locally on the APA 320 and/or one or more of the input devices 314. When all or portions or subsets of the data in the storages 342 are maintained at multiple locations, the APA 320 may periodically implement a synchronization operation to ensure that the multiple copies remain common with one another, such as through replication or distributed transactions.

The input devices 314 may collect programming information, such as a patient profile, when the input devices 314 have network connectivity, either transparently or on demand. For example, a wireless connection may be maintained with the programming device 304, alternatively, the programming device 304 may be afforded network connectivity when the device 304 is docked or cradled in the docking station. Programming data may be exported from the programming device 304, through the APA 320 and stored in the storage 342. Alternatively, programming data may be exported from the programming device 304 through the use of a media card that is removed from the programming device 304 and loaded into another computer connected to the storage 342 such as the APA or another user interface 346.

Figure 3B:
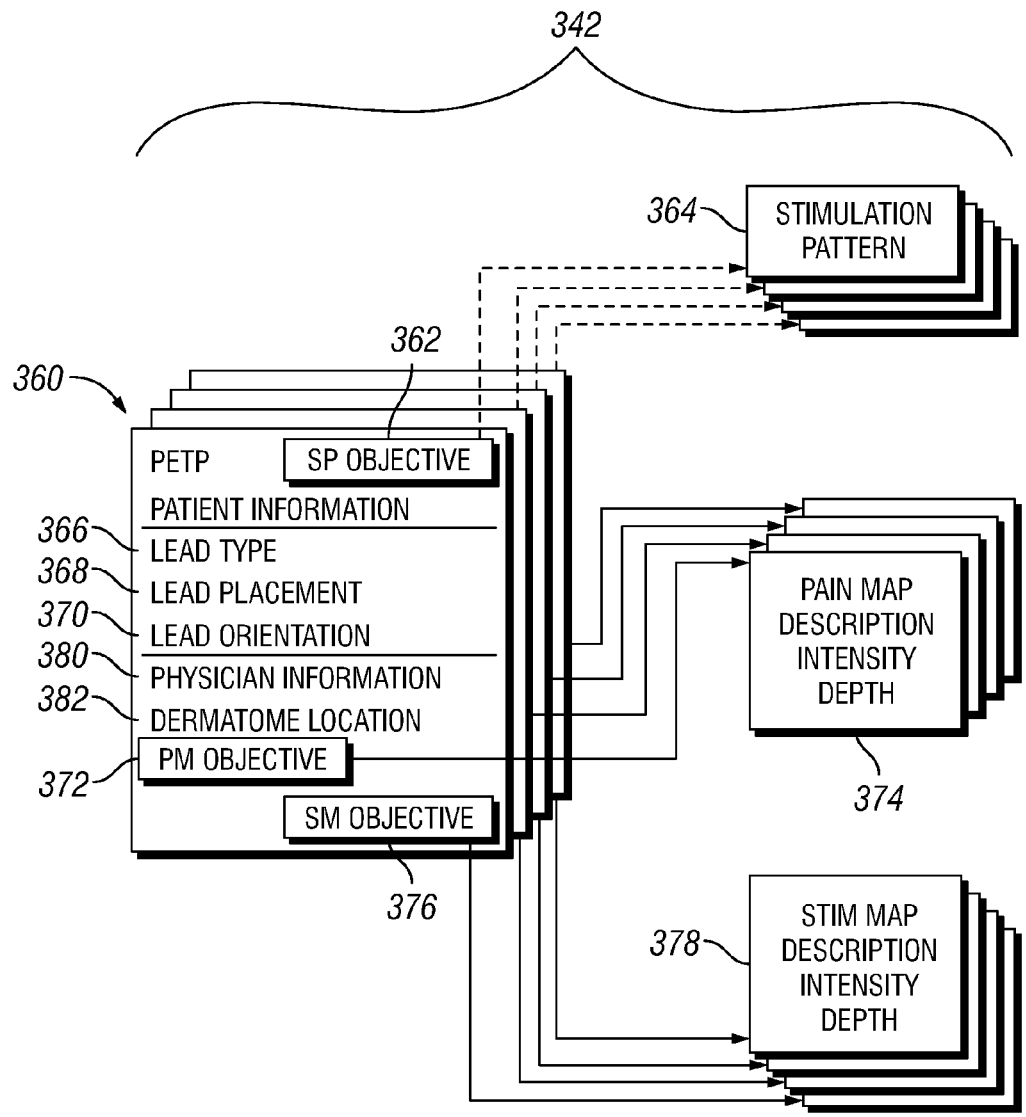
FIG. 3B illustrates an example of a pre-existing therapy profile that may be collected by the APA and saved in the shared database.

FIG. 3B illustrates an example of the information that may be saved in the storage 342. The storage 342 stores a collection of pre-existing therapy profiles (PETP) 360, each of which has a stimulation pattern object 362 mapping the PETP 360 to one or more stimulation programs or patterns 364. The pre-existing patient profiles 360 have at least one of a prior lead type 366, a prior lead placement 368, and a prior lead orientation 370. The PETP 360 include a pain map object 372 that maps the PETP 360 to one or more pain maps 374 that have been previous entered for the corresponding patient. The PETP 360 include a stimulation map object that maps the PETP 360 to one or more stimulation maps 378 that have been previous entered for the corresponding patient. Optionally, the PETP 360 includes physician information 380 and one or more prior dermatome locations 382 for the prior patient.

The PETPs 360 may be recorded from new patient implants and/or created from models. Optionally, the PETPs 360 may be created by going back through past implant records and analyzing these records to derive the above listed therapy profile information.

The APA 320 includes one or more processors that may separately or in a shared manner, implement various operations described throughout ion in connection with maintaining the database and programming of the neurostimulator.

Next, the structure and operations of system 300 will be described in connection with using the database of pre-existing therapy profiles to assist a clinician in programming a neurostimulator.

The APA 320 includes a comparator module 322 and a candidate module 324, as well as local storage areas denoted at 326-328. The reference numeral 326 denotes a new patient profile. Reference numeral 327 denotes a rating table built by the APA 320 based on comparisons of new and prior patient profiles. Reference numeral 328 denotes a list or group of candidate therapy profiles that have been identified by the APA 320 to be suggested to a clinician for programming the neurostimulator 302. As explained below in more detail, the comparator module 322 compares the new patient profile with at least a subset of the collection of pre-existing patient profiles and derives (e.g., similarity ratings and overlap scores) therefrom in connection with each previous patient profile. The candidate module 324 reviews the profile matching scores and forms a list of candidate therapy profiles based on the profile matching scores and match thresholds. For example, the candidate module 324 includes on the list of candidate therapy profiles, any pre-existing therapy profiles that have a profile matching score that satisfies a match threshold.

As explained below in more detail, the comparator module 322 utilizes multiple matching functions to form numerical representations of similarity ratings and overlap scores between the new patient profile and the pre-existing patient profiles. More specifically, the comparator module 322 may utilize a matching function to a similarity rating between planned lead placement and prior lead placements. The comparator module 322 may utilize a matching function to form a similarity rating between planned lead type and prior lead type. Alternatively, or in combination, the comparator module 322 may utilize another matching function to form an overlap score between new and prior pain maps. Alternatively, or in combination, the comparator 322 may utilize matching functions to form a similarity rating between planned or prior lead orientations.

The comparator module 322 builds the ratings table 327 based on the foregoing comparisons. The ratings table 327 maintains a list of indices 325 to each PETP that has been analyzed. Each PETP index 325 is mapped in a one to one relation with each feature that is compared. For example, the ratings table 327 may map each PETP index 325 to a corresponding lead similarity rating 323, a pain overlap score 321, and a stimulation overlap score 319.

The candidate module 324 creates a list of candidate PETPs 328 based on the ratings and overlap scores in the ratings table 327. For example, the candidate module 324 uses the various similarity ratings and/or overlap scores that are determined by the comparator module 322 to identify the subset of potential pre-existing patient profiles that best resemble the new patient profile. This subset of potential pre-existing patient profiles is then used to produce the list of candidate therapy profiles 328.

The storage 342 may represent one or more databases or other types of storage architectures. The storage 342 stores patent records, physician records, patient profiles, therapy profiles, and the like. The storage 342 stores a collection of pre-existing therapy profiles derived from prior actual patients or patient models.

Figure 4:
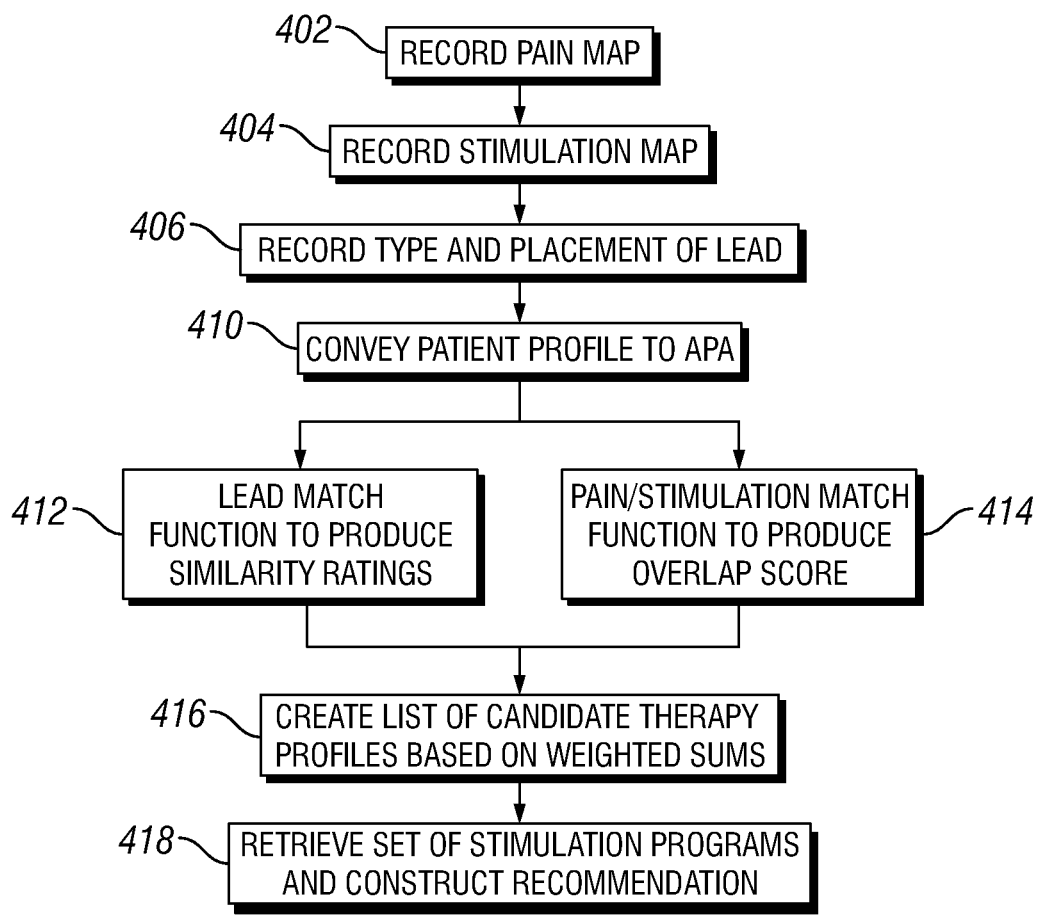
FIG. 4 illustrates a flow chart to implement a candidate therapy search in accordance with an embodiment.

FIG. 4 illustrates a flow chart implemented in accordance with an embodiment to assist in neurostimulation programming. Beginning at 402, the process records a new pain map. The pain mapping operation may be performed prior to lead implantation as part of a surgical planning process. During the pain mapping operation, the clinician and/or patient may enter pain information in various manners.

Figure 5:
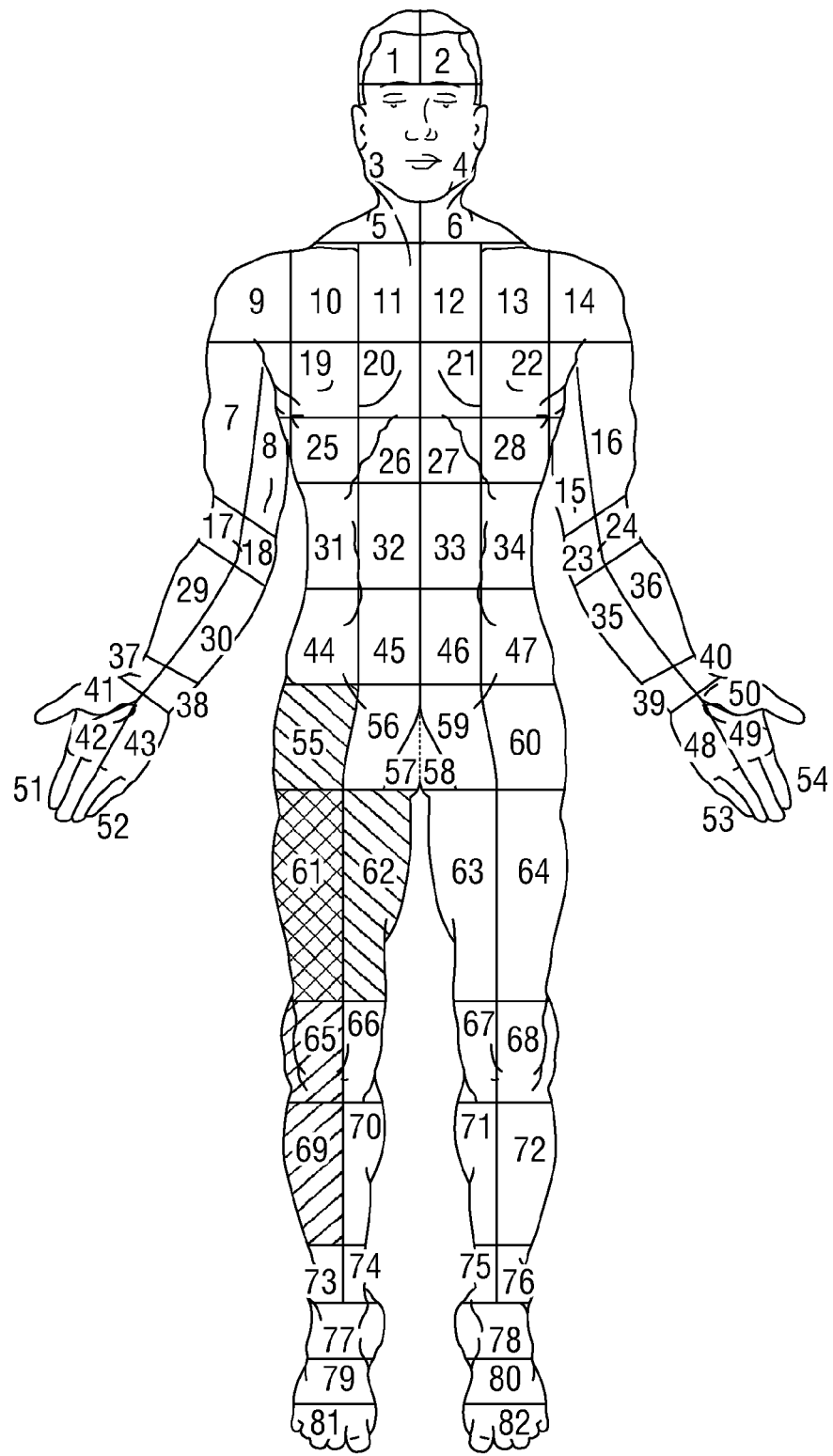
FIG. 5 illustrates a pain map as an anterior anatomical view of a human image in a prone position with an exemplary set of regions divided in accordance with an embodiment.
Figure 6:
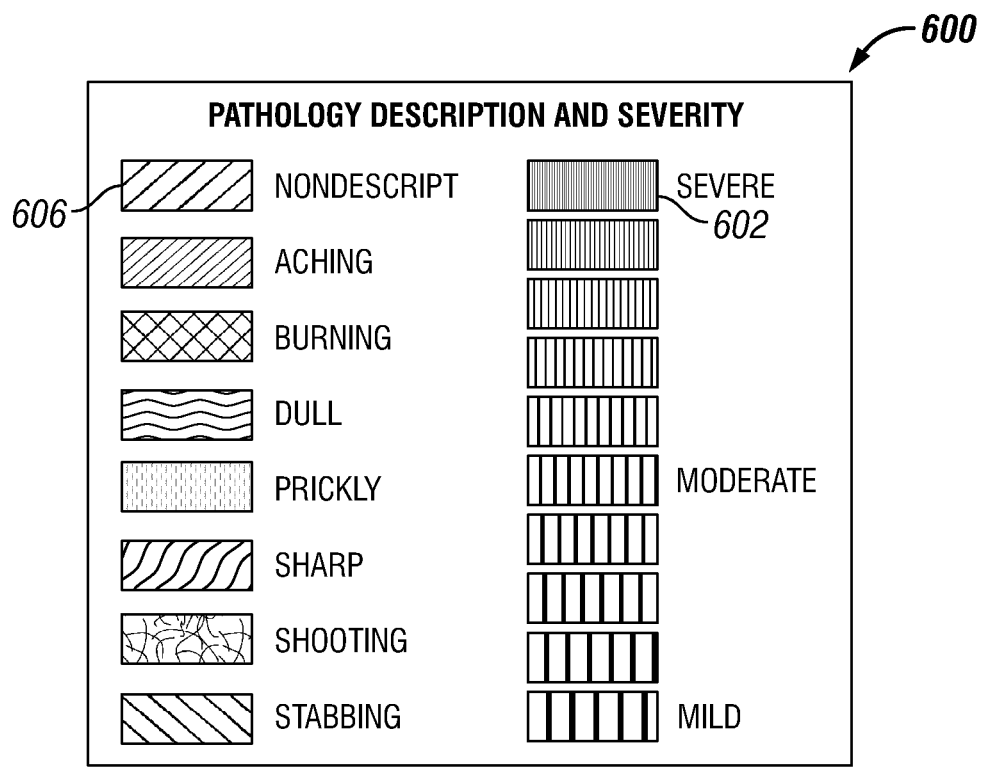
FIG. 6 illustrates an example of a pathology pop-up window 600 that may be presented to a clinician to record pain map information.

FIG. 5-6 illustrates one exemplary implementation by which a pain map may be recorded at 402 as well as when forming the PETPs 360. Any one or more of the input devices 314 (FIG. 3A) may be used to enter one or multiple pain maps for the patients. By way of example only, the clinician may use a programming device 304 to enter the pain map. For example, the clinician may select a "pain map creation" option by choosing an icon, menu option, button, input field and the like. The programming device 304 may then display, on the programming device 304, one or multiple anatomical models of a human showing a posterior view, an anterior view, a side view and the like. Optionally, the anatomical model may illustrate the human standing, sitting or lying down. The anatomical model may be divided into numbered regions.

FIG. 5 illustrates an anterior anatomical view of a human image in a prone position with an exemplary set of regions. While the image of FIG. 5 is shown in two-dimensions, it is entirely appropriate that the user be presented three-dimensional images. In the preparation of any such three-dimensional images, it may be necessary to combine two objects (e.g., an anterior view of a subject and a posterior view of the subject).

FIG. 5 illustrates only a portion of the total available regions. Optionally, anterior and posterior views may be shown simultaneously which include additional regions. The number of regions may be arbitrarily determined based on the object, the substantive information to be conveyed or represented by the regions, and the graphical manner used to convey relevant conditions assignable to the regions. The "conditions" used to define the nature of the pain attributed to a specific region may include one or more of: type, intensity and depth. "Type" refers to a perceived character of the pain. "Intensity" refers to a perceived degree of pain. "Depth" refers to a perceived physical level of pain, i.e., surface to bone.

The type, intensity and depth attributes may be given independent visual characteristics in order that the attributes of any given region may be readily discernable from only a visual inspection. For example, "type" may be evidenced by a texture or pattern, and "intensity" may be communicated by a change in color (e.g., hue, shade, etc.) "Depth" may be illustrated by shadowing a subject region to create the illusion a different physical level. By providing each of the conditions with independent visual characteristics, the system may simultaneously convey each of the conditions attributed to any region. The specific feature (e.g., colorization, pattern, etc.) used to convey a particular characteristic may vary.

FIG. 6 illustrates an example of a pathology pop-up window 600 that may be presented to a clinician when recording a pain map. The window 600 illustrates a list of pain descriptor options 606 and a list of pain severity options 602. The clinician or patient may choose from lists 602 and 606 to describe a particular type of pain. For example, a pain may be described as moderate and to have a "burning" sensation. Alternatively, the pain may be describes as a mild "aching" feeling. Optionally, the clinician may be afforded another type of input window to describe the severity and type of pain.

Once one or more pain maps are creates for the current patient, the input device 314 (FIG. 3A) conveys the pain map(s) to the APA 320 over a corresponding one of links 310-312 through the Internet 318. The APA 320 stores the pain map locally as part of the new patient profile 326.

Returning to the process of FIG. 4, at 404, a stimulation map may be recorded in connection with the new patient. The process carried out in connection with recording a stimulation map may be similar to the process for recording a pain map as discussed above in connection with FIG. 5-6. For example, once a lead is implanted, the clinician may apply a stimulation pattern and ask the patient to describe the location at which the patient feels the effect of the stimulation pattern. The patient may also describe the type and severity of stimulation. The clinician may then enter the location, type and severity of the effect using a graphical user interface such as illustrated above in connection with FIG. 5-6. Optionally, the stimulation map may be recorded before, during or after lead implantation to collect and record one or more stimulation maps.

Once one or more stimulation maps are creates for the current patient, the input device 314 (FIG. 3) conveys the stimulation map(s) to the APA 320 over a corresponding one of links 310-312 through the Internet 318. The APA 320 stores the stimulation map locally as part of the new patient profile 326.

At 406, the process records a planned or new lead attributes such as lead type, lead orientation, lead placement, electrode configuration and the like. The planned or new lead type, orientation and placement may correspond to a lead that has already been implemented or has not yet been implanted but is intended to be implemented with a current patient. Any one or more of the input devices 314 (FIG. 3A) may be used to enter the planned or new lead type, orientation and placement for the current patient through a graphical user interface. By way of example only, the clinician may use a programming device 304 to enter the planned or new lead type, orientation and placement. For example, the clinician may select a "lead type/placement" option by choosing an icon, menu option, button, input field and the like. The programming device 304 may then display, on the programming device 304, one or multiple virtual leads and anatomical models of a human or portions of a human showing a posterior view, an anterior view, a side view and the like.

Figure 7A:
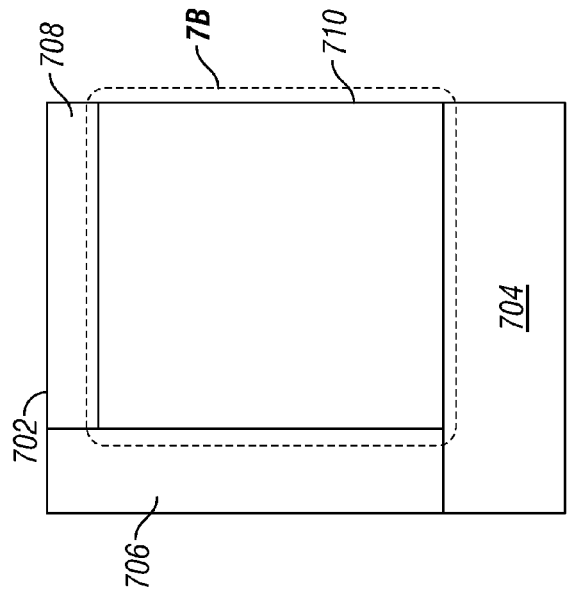
FIG. 7A-7C illustrates a graphical user interface to record lead attributes in accordance with an embodiment.
Figure 7C:
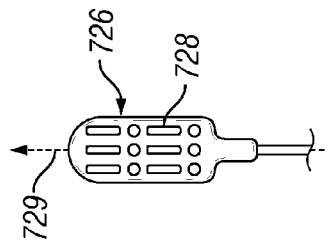
Figure 7B:
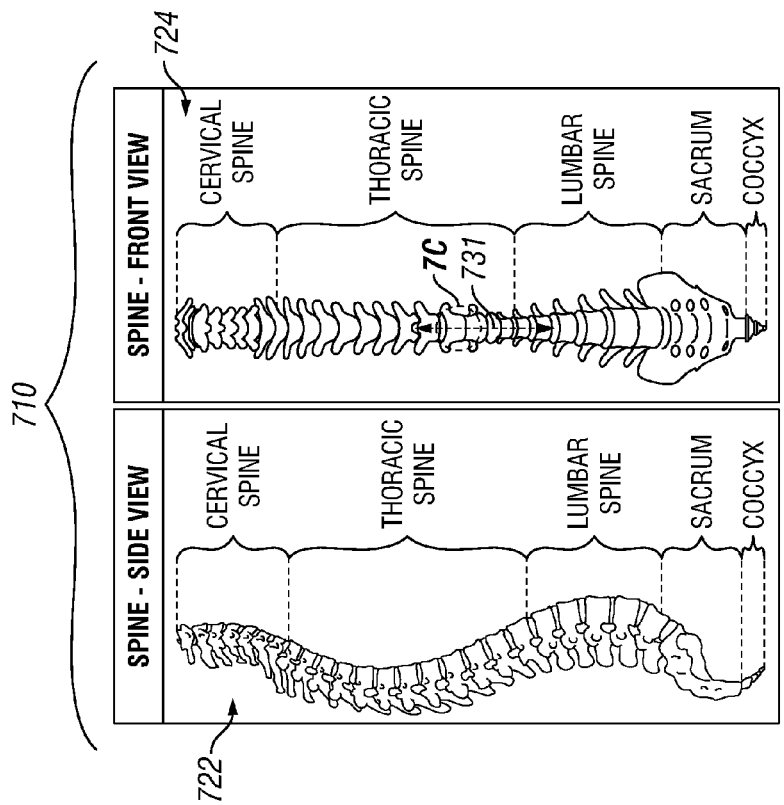

FIG. 7A-7G illustrates exemplary displays that may be presented on one of the input devices 304 to the clinician in order to record a planned lead type, orientation and placement for a new patient. FIG. 7A-7C illustrates a graphical user interface (GUI) 702, such as presented on a programming device 304, PC 306 or laptop computer 308. For example, the GUI 702 may represent a touch sensitive display or simply a computer screen that is controlled through a mouse and keyboard or other user input mechanism. The GUI 702 includes a data entry area 704, a lead attribute area 706, a patient information area 708 and a patient planning area 710. Each of the areas 704-710 may be touch sensitive, and/or include hard keys, knobs, soft knobs, buttons and the like. The data entry area 704 may display various fields, in which the clinician enters patient profile information, commands and other data. The lead attribute area 706 may present a set and subset of different types of leads, electrode configurations, lead locations, lead orientations, electrode locations, electrode orientations, lead body shape and other lead attributes to facilitate entry of a planned lead type, orientation and lead placement. Patient information area 708 may designate basic information about the patient (e.g., age, weight, height, gender, etc.).

The planning area 710 may be used to graphically enable the clinician to enter the planned lead type, orientation and lead placement. For example, the planning area 710 may display a virtual lead that is shaped and sized based on the selection from the lead attribute area 706. The planning area 710 may also display a graphical representation of an anatomy of interest. The graphical representation of the anatomy of interest may be a model of a generic anatomical structure (e.g., a generic spine, generic organ). The model may be sized and shaped based on the patient's information (e.g. weight and height). The graphical representation of the anatomy of interest may be an actual image of the current patient where the image is obtained from a diagnostic imaging system such as an ultrasound system, computed tomography (CT) system, X-ray system, magnetic resonance imaging system, positron emission tomography system, nuclear medicine system and the like. Alternatively, the graphical representation of the anatomy of interest may be a model that is created based upon patient specific information about the particular patient.

A clinician may use the GUI 702 to position a virtual lead on the patient anatomy at a position representative of a planned location at which an actual lead was implanted or is planned to be implanted in a new patient. The planning area 710 is illustrated with examples of side and back views of spine models. The spine is shown from a side view 722 and a back view 724. The clinician may select one or more vertebrae from the side or back views 722 and 724 by touching on the desired vertebrae or double clicking on a select vertebrae or group of vertebrae. Once a select vertebrae or group of vertebrae are chosen, the planning area 710 may show an enlarged view of the select subset of vertebrae.

The select subset of vertebrae may be displayed in various manners to facilitate designation by the clinician of the positioning and orientation of the electrodes.

The planning area 710 may facilitate lead placement by displaying a single coordinate marking the center of the lead. Optionally, the planning area 710 may permit lead placement by displaying two coordinates marking each extremity or multiple coordinates marking various locations on the lead. The lead orientation can be derived from two or more coordinates. Using more than two coordinates also allows the recording of lead curvature when applicable. Lead curvature may be used optionally in the lead location matching function.

FIG. 7D-7G illustrates different exemplary two-dimensional and three-dimensional views of subsets of vertebrae or a single vertebra that may be presented as a graphical representation of patient anatomy. The clinician may use a mouse or a touch sensitive display to "grab" a lead, drag the lead to a desired location and drop or release the lead upon the select vertebrae. The electrodes of the lead are then overlaid upon the graphical representation of the spine.

Figure 7D:
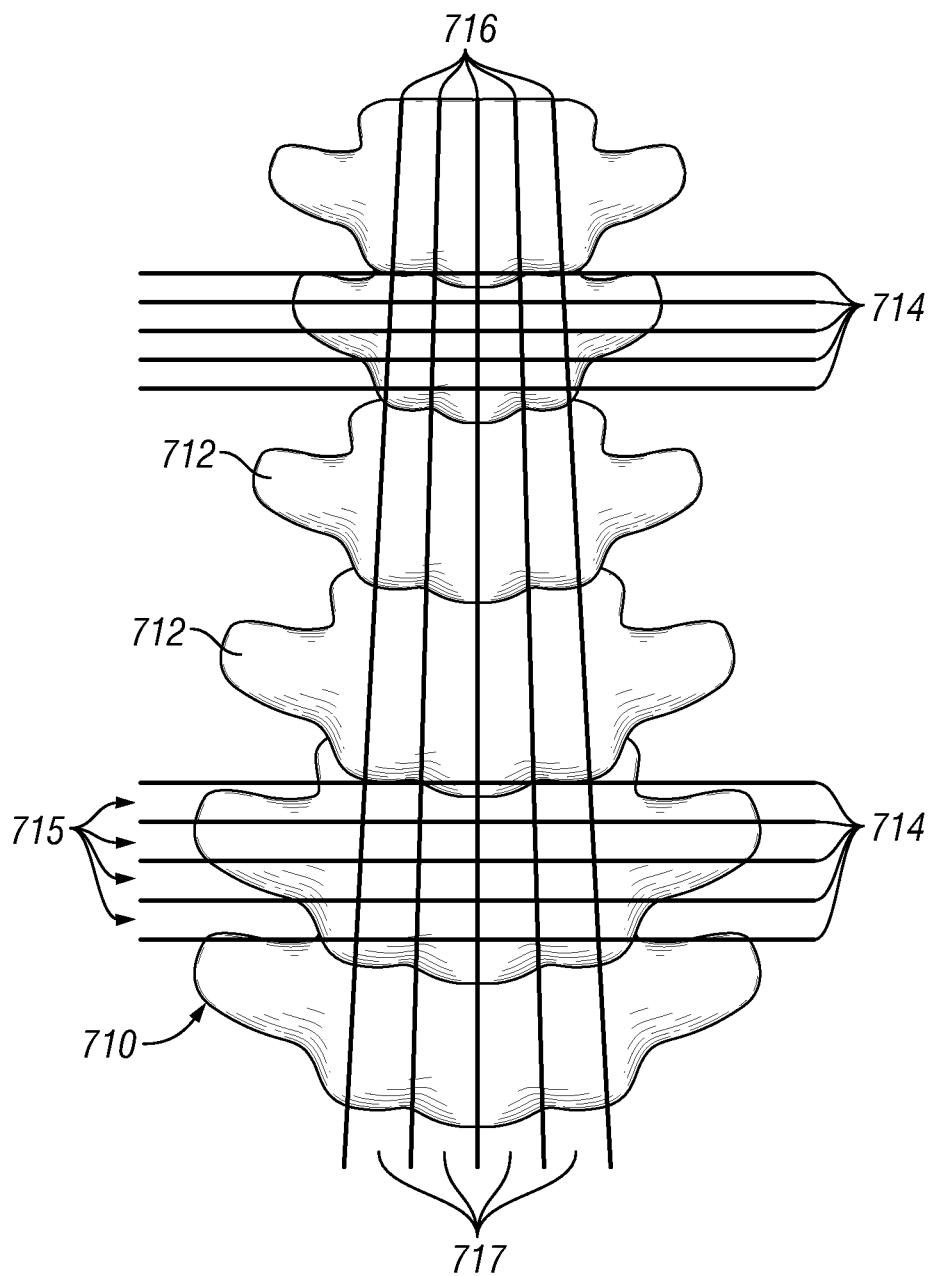
FIG. 7D illustrates an exemplary a display that may be presented to a clinician.
Figure 7E:
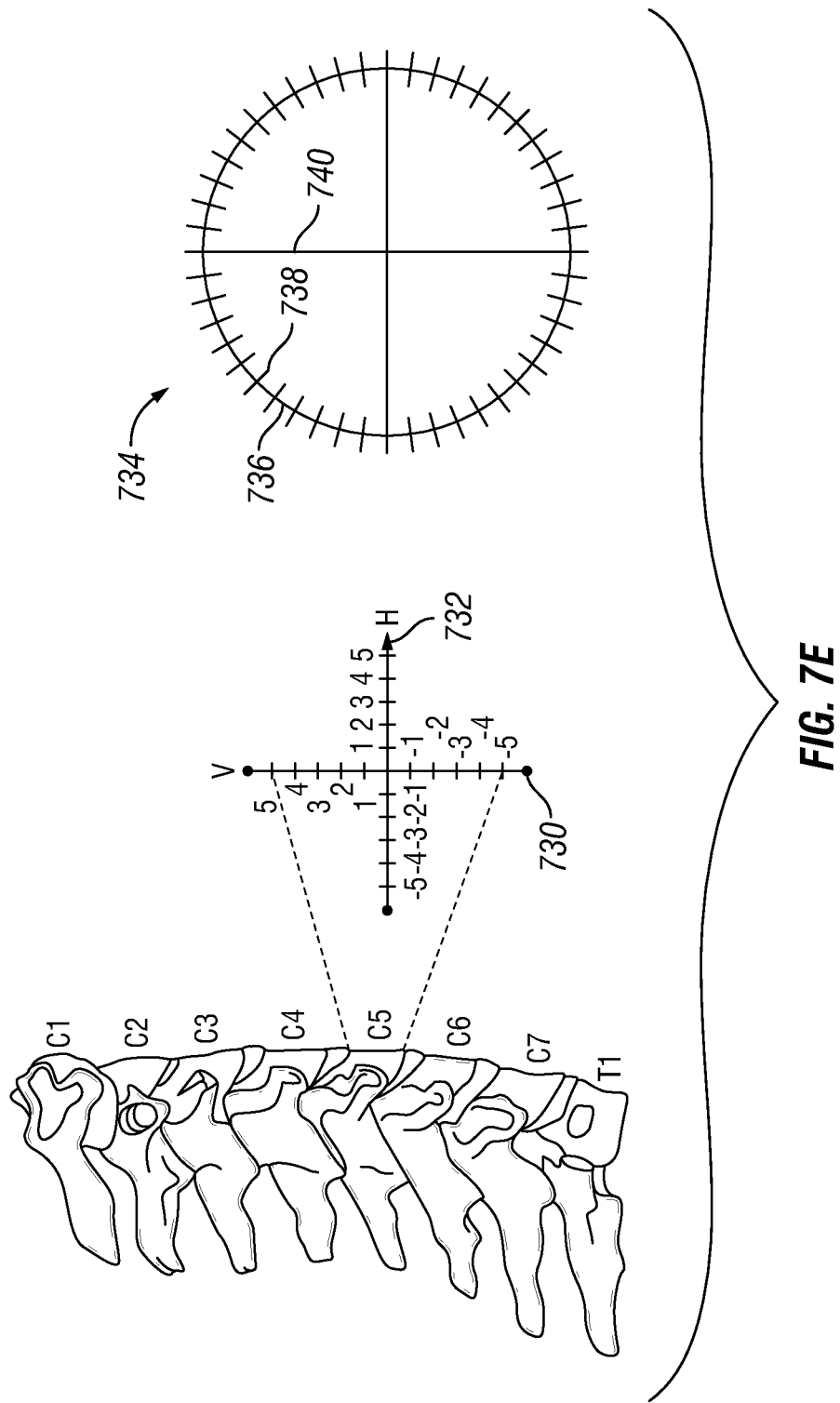
FIG. 7E illustrates an alternative example of graphical information presented in the planning area of the GUI.

FIG. 7D illustrates an exemplary a display that may be presented to a clinician. The display presents a graphical representation of an anatomy of interest 710. The GUI 702 (FIG. 7A-7C) permits the clinician to position and/or orient a virtual lead on the anatomy of interest at a position or orientation representative of a planned location at which an actual lead was implanted in the new patient. The display displays, as the anatomy of interest, a virtual representation of a series of vertebra 712. The GUI 702 permits the clinician to locate electrodes of a virtual lead at a desired horizontal, vertical or orientation alignments on the planned location. The display presents horizontal markers 714 and vertical 716 relative to the anatomy of interest 710. The markers 714 and 716 subdivide the anatomy of interest 710 into multiple sections 715 and 717, respectively. The GUI 702 permits a clinician to enter the planned lead attribute relative to the markers 714 and 716 to designate a position at which an actual lead was implanted in the new patient.

In the example of FIG. 7D, the markers 714 and 716 may be presented in a non-linear scaled manner proportioned to a size of the anatomy of interest. For example, a single vertebra of all patients may be divided using a constant number of markers 714 and 716. In the example of FIG. 7D, the three to four horizontal markers 714 are used per vertebra, while six vertical markers 716 are used per vertebra. In this example, the same number of markers is used on all patients regardless of the size of the patient. Hence, a large patient (with large vertebra) will have each vertebra divided into the same number of sections as a small patient (with small vertebra). When markers are presented in a non-linear scaled manner, this effectively decouples lead placement from the size of the anatomy of interest.

Alternatively, the markers may be presented in a linear scaled manner such that a larger sized anatomy of interest will include more markers, while a smaller sized anatomy of interest will include fewer markers.

As a further example, the clinician may use data entry fields to enter specific horizontal and/or vertical coordinates for the electrodes or lead. The horizontal and/or vertical coordinates may be designated relative to a reference point on a select one or more of the vertebra. For example, with reference to FIG. 7E, the user may select the C5 vertebrae. Once the C5 vertebra is selected, horizontal and vertical line segments 732 and 730 may be displayed. The line segments 732 and 730 have distance markers located there along to designate subdivisions vertically and horizontally from an origin or center point on the C5 vertebra. The clinician may then enter the location of the electrodes, in the vertical alignment on the planned location, such as by clicking on or typing in the numeric marker for the desired position along the vertical line segment 730. In example of FIG. 7E, the vertical line segment 730 has a central mark denoted as 0 with positive and negative numeric values increasing and decrementing.

The line segments 730 and 732 subdivide each vertebra across multiple sections in both lateral (x) and longitudinal (y) axes. A constant number of subdivisions may be used per vertebra (e.g. 5, 10, etc.). Different patients will have different size vertebra. When a constant number of subdivisions are used for all patients, this yields a non-linear scale that is proportional to the size of the patient and the size of each vertebral body. Utilizing a constant number of subdivisions per vertebra, will partly decouple the lead placement from variations in patient dimensions. Utilizing a constant number of subdivisions per vertebra would also facilitate recording of the approximate placement of the lead. Hence, this process accounts for variations in patient dimensions. By selecting a point along the vertical and horizontal line segments 730 and 732, the clinician may indicate the vertical and horizontal alignment of the electrode or lead with respect to the horizontal and vertical center of the C5 vertebra.

In an alternative embodiment, the numeric values may be a linear fixed distance apart, such that by designating an electrode at the vertical position 2 this indicates that the electrode was positioned 2 mm above a center point along the vertical line segment 730. The horizontal line segment 732 has distance notations as well that may represent 1 mm spacing.

An orientation compass 734 may also be presented to the clinician in the planning area 710. The compass 734 includes a rotation line segment 736 with markers 738 provided along the segment 736. The markers 738 denote degrees of rotation with respect to a predetermined axis, such as a longitudinal axis 740 of the spine.

Figure 7F:
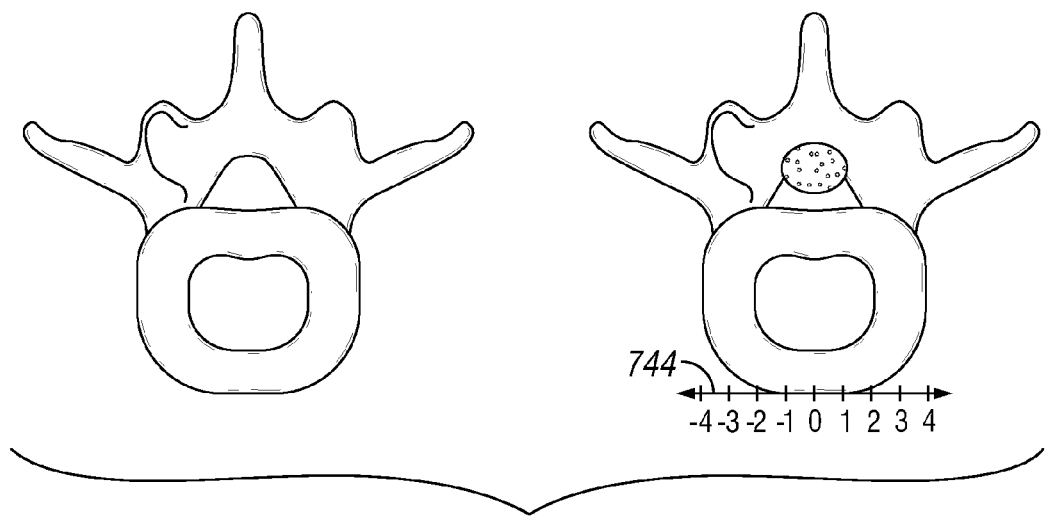
FIG. 7F illustrates an alternative example of graphical information presented in the planning area of the GUI.

FIG. 7F illustrates an alternative example of an anatomical model that may be presented to the clinician when entering lead placement and orientation. FIG. 7F illustrates a top view of a lumbar vertebra. The clinician may designate the horizontal alignment by selecting a point along horizontal axis 744.

Figure 7G:
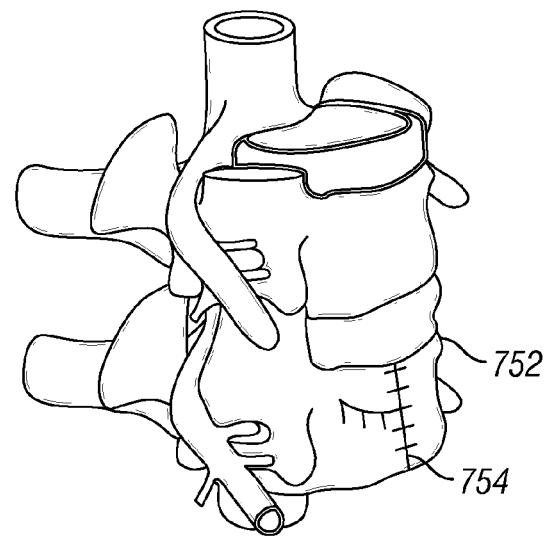
FIG. 7G illustrates an alternative example of graphical information presented in the planning area of the GUI.

FIG. 7G illustrates an alternative example of an anatomical model. FIG. 7G illustrates a three-dimensional representation of two vertebrae. The clinician may designate the vertical and horizontal alignment of the electrodes by selecting points along the horizontal and vertical segments 752 and 754.

In any of the graphical representations of FIG. 7A-7F, the user may also click upon and drag the vertebrae to rotate the vertebrae along a vertical or horizontal rotational axis. Rotating the anatomical model may afford easier designation for lead placement and orientation.

Returning to FIG. 7A-7C, a virtual lead 726 is illustrated in the planning area 710. The virtual lead 726 will be shaped and sized to match the type of lead designated by the clinician in lead attribute area 706. In the example of FIG. 7A-7C, the virtual lead 726 has an array of electrodes 728 organized into 3 columns. The clinician positions the virtual lead 726 on the graphical representation of the desired vertebra. The clinician may then designate the horizontal and vertical alignment of the virtual lead 726 relative to horizontal and vertical reference points utilizing one of the alignment mechanisms discussed above. Optionally, the clinician may designate the orientation of the virtual lead 726 utilizing the compass 734 or another orientation mechanism. The orientation of the virtual lead 726 is indicated relative to a lead longitudinal axis 729 and relative to a spinal longitudinal axis 731 to thereby indicate the orientation at which an actual lead was implanted or is planned to be implanted.

Once the lead type, placement and orientation are entered for the current patient, the input device 314 (FIG. 3) conveys the lead type, placement and orientation data to the APA 320 over a corresponding one of links 310-312 through the Internet 318. The APA 320 stores the lead type, placement and orientation locally as part of the new patient profile 326.

Optionally, the input device 314 may build a complete new patient profile by holding the pain map, stimulation map and the lead type, placement and orientation data until all such information has been entered by the clinician. Thereafter, at 410, the information collected at 402-406 may be combined to form a complete new patient profile that is then conveyed to the APA 320 (FIG. 3) at once.

At 412 and 414, the APA 320 accesses one or more storage 342 that contain the pre-existing therapy profiles 360 (FIG. 3B), and the APA 320 implements matching functions. The matching functions compare information from the new patient profile 326 collected at 410 with information in the pre-existing therapy profiles 360 stored in storage 342. At 412, the matching function may implement a comparison of lead-related information where the comparison may be based on one or more of lead type, lead placement and lead orientation. At 414, the matching function may implement a comparison of pain and/or stimulation related information where the comparison may be based on one or more pain maps and/or stimulation maps.

The matching functions at 412 and 414 produce similarity ratings, pain overlap scores and stimulation overlap scores that are numeric values representing an amount or degree of similarity between the new and prior lead, pain and stimulation related information in the new patient profile 326 and the PETPs 360.

$$\psi=\{L,P\}$$

$$f_{match}(\psi_1,\psi_2)=W_L f_{L,match}(L_1,L_2)+W_P f_{P,match}(P_1,P_2)$$

A match function $f(\psi)$ is used that produces a numerically rating that represents the similarity between the new patient profile and a corresponding one of the pre-existing patient profiles stored in the storage 342. The matching functions 412 and 414 include two sub-matching functions ($f_{L,match}$) and ($f_{P,match}$) that represent lead similarity (L) and pain/stimulation map scores (P) respectively. For example, if the lead-related information in the new patient profile 326 is compared with the lead-related information in 50 PETPs 360, the match function will create 50 lead similarity ratings, one for each of the 50 PETPs 360. If the pain-related information in the new patient profile 326 is compared with the pain-related information in 100 PETPs 360, the matching function will create 100 pain overlap scores and stimulation overlap scores, one for each of the 100 PETPs 360. For each comparison of the new patient profile with a PETP, the process combines the similarity ratings, pain overlap scores and stimulation overlap scores using a weighted sum to generate a profile matching score for the current PETP and the new patient profile.

Once similarity ratings, pain overlap scores and stimulation overlap scores for all or subset of potential pre-existing therapy profiles are identified at one or both of 412 and 414, and profile matching scores for the all of the PETPs are created, flow moves to 416. At 416, the process creates a list of candidate therapy profiles (CTPs) 328 (FIG. 3A). The list of CTPs 328 may be displayed to the clinician on an input device 314, such as the programming device 304. The clinician then chooses from the list of CTPs 328 to select a stimulation program.

Figure 8:
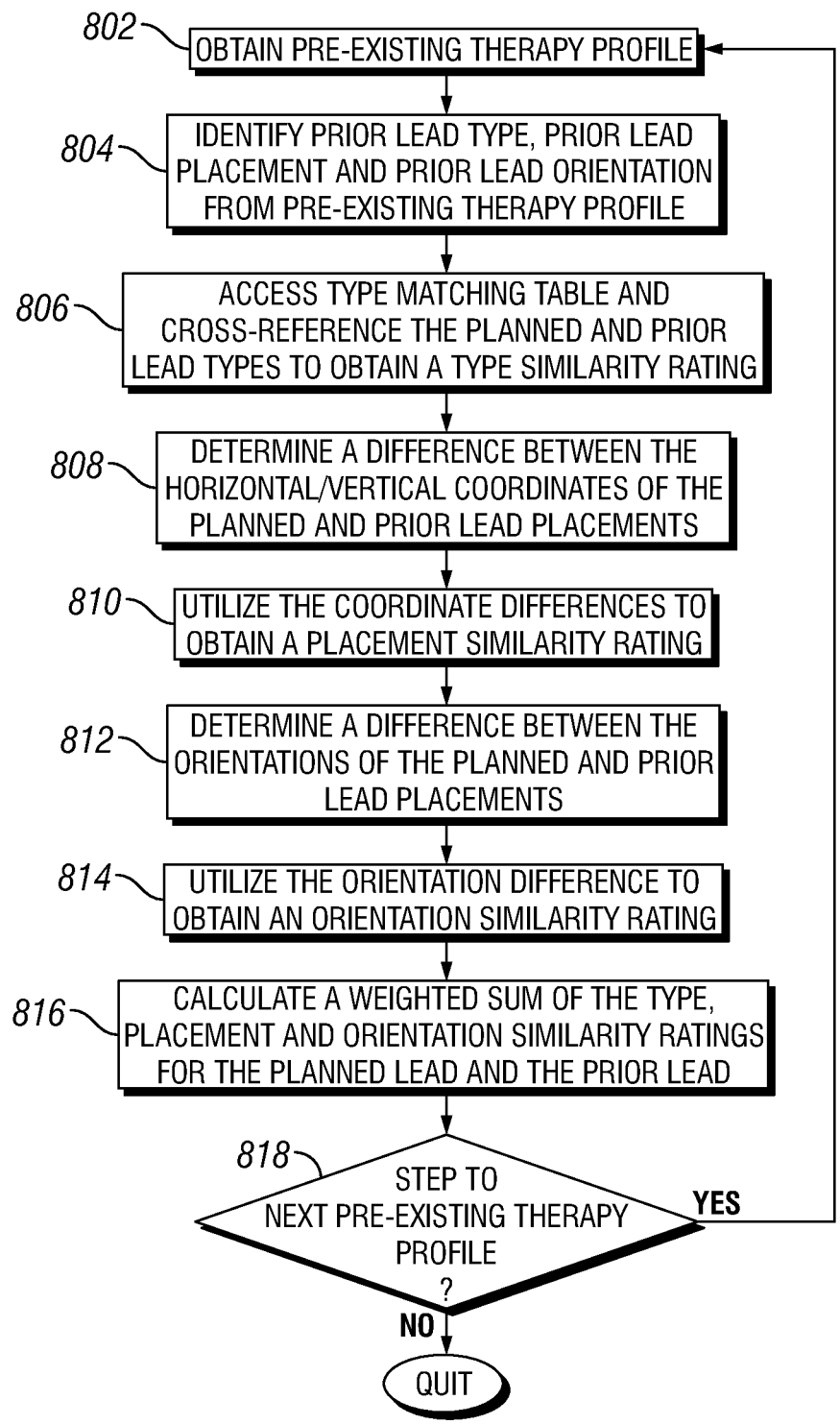
FIG. 8 illustrates a lead matching function that may be implemented in accordance with one embodiment.

FIG. 8 illustrates a lead matching function that may be implemented by the comparator module 322 in accordance with one embodiment. The process of FIG. 8 seeks to assign similarity ratings to one or more lead attributes of interest. By way of example only, the attributes of interest may be lead type, lead placement and lead orientation. Optionally, other lead attributes may be of interest and thus compared to derive individual attribute similarity ratings between new and prior leads. In the present exemplary embodiment, the lead matching function ($f_{L,match}$) is calculated based on the lead type ($L_{Type}$), relative location ($L_{Loc}$), and orientation ($L_\Theta$) as follows:

$$f_{L,match}(L_1,L_2)=W_{Type}f_{Lead-Type,match}(L_{Type,1},L_{Type,2})+ \\ W_{Loc}f_{lead-loc}(L_{loc,1},L_{Loc,2})+W_{Lead-\Theta}f_{lead-\Theta}(L_{\Theta,1},L_{\Theta,2})$$

Beginning at 802, a PETP 360 is obtained from storage 342. At 804, a prior lead type, placement and orientation are identified from the PETP 360 that was obtained at 802. At 804, a type matching function is accessed and the prior lead type and new lead type are cross-referenced with one another into the type matching function. By way of example, the lead type matching function may be a lookup table that returns a numerical value representing a normalized distance between the two lead types.

The lead type matching function may be expressed as follows, where $L_{Type,1}$ and $L_{Type,2}$ represent the new and prior lead types, and $\Delta T[L_{Type,1}, L_{Type,2}]$ represents a two-dimensional table of similarity rating:

$$f_{Lead-Type,match}(L_{Type,1}, L_{Type,2}) = \Delta T[L_{Type,1}, L_{Type,2}]$$

$$\Delta T = \begin{bmatrix} \Delta T_{1,1} & & \\ & \Delta T_{i,j} & \\ & & \Delta T_{N,N} \end{bmatrix}$$

FIG. 9 illustrates an exemplary type matching table 900 that includes lead types along the rows 902 and lead types along the columns 904. The rows 902 may correspond to the new or planned lead type, while the columns 904 may correspond to the prior lead type pulled from the PETP 360. The table 900 includes cells 906 at the intersections of the rows 902 and columns 904. Each cell 906 includes a similarity rating (e.g. between 0 and 10). A low rating indicated that the two lead types are very different, while a high rating indicates that the two lead types are very similar. A "0" rating is for lead type pairs that are completely incomparable and a "10" rating is for lead type pairs that are interchangeable or identical. For example, the lead type #1 has a similarity rating of "7" with the lead type #7. Returning to FIG. 8, at 806, a type similarity rating is returned from the table 900.

At 808, the process determines a difference between one or more of horizontal/vertical placement coordinates at which the new and prior lead placements were located on the anatomy of interest relative to the markers. For example, the symbol ΔX may represent the difference in horizontal placement between X1 and X2 placement markers of the new and prior leads, respectively. As a further example, if the new lead is horizontally placed at the marker X1=2 and the prior lead is placed at marker X2=1, then the difference in horizontal placement ΔX would be ABS[2−1]=1. The symbol ΔY may represent the difference in vertical placement between Y1 and Y2 placement markers at the new and prior leads, respectively. As a further example, if the new lead is vertically placed at marker Y1=−2 and the prior lead is placed at marker Y2=1, then difference in horizontal placement ΔX would be ABS[(−2)−1]=3.

As explained above, the lead placement is recorded relative to anatomical structures. The lead placement and orientation matching functions may be based on single lead coordinates and expressed as follows, where $L_{loc-x,1}$, and $L_{loc-x,2}$, represent the new and prior lead horizontal coordinates; $L_{loc-x,1}$, and $L_{loc-x,2}$, represent the new and prior vertical coordinates; $L_{loc,1}$, $L_{loc,2}$ represent the new and prior lead overall placements; $L_{loc-\Theta,1}$, and $L_{loc-\Theta,2}$, represent the new and prior lead orientations with respect to a first axis; and $L_{\Theta,1}$, and $L_{\Theta,2}$ represent the new and prior lead overall orientation.

$$f_{lead-loc}(L_{loc,1}, L_{Loc,2}) = \frac{1}{e^{[(L_{loc-x,1}, -L_{Loc-x,2})^2 + (L_{loc-y,1}, -L_{Loc-y,2})^2]^{1/2}}}$$

$$f_{lead-\theta}(L_{\theta,1}, L_{\theta,2}) = \frac{1}{e^{\wedge} ABS(L_{loc-\theta,1}, -L_{Loc-\theta,2})}$$

At 810, the process utilizes the horizontal/vertical placement differences ΔX and ΔY to obtain a placement similarity rating. For example, the placement similarity rating may represent a distance D=square root (ΔX²+ΔY²). The lead location matching function at 808 and 810 returns a numerical representation of the placement similarity rating or proximity between the new and prior pair of leads.

At 812, the process determines an orientation angle Θ1 between a lead orientation reference axis of the new lead and an anatomy reference axis (such as the horizontal or vertical axes on the compass 734 in FIG. 7D) of the anatomy of interest. At 812, the process also determines an orientation angle Θ2 between a lead orientation reference axis of the prior lead and the reference axis of the anatomy of interest. For example, the new lead may be placed at an orientation angle Θ1=45 degrees clockwise from the vertical reference axis, while the prior lead was placed at an orientation angle Θ2=40 degrees clockwise from the vertical reference axis.

At 814, the process utilizes the new and prior orientation angles Θ1 and Θ2 to obtain an orientation similarity rating ΔΘ. For example, the orientation similarity rating may represent an absolute value of the angular difference between the new and prior orientation angles, ΔΘ=ABS(Θ1−Θ2). The lead orientation matching function at 812 and 814 returns a numerical representation ΔΘ of the orientation similarity rating between the new and prior pair of leads. As an example, if the new lead is oriented at Θ1=−25, and the prior lead is oriented at Θ2=10, then similarity rating may be ΔΘ=ABS(Θ1−Θ2)=ABS[(−25)−10]=35.

Optionally, the lead placement and orientation matching functions may be based on pairs of lead coordinates for each lead. Alternatively, the lead placement and orientation matching functions may be based on three-dimensional sets of lead coordinates for each lead.

The process may be repeated to compare other lead attributes and to derive attribute similarity ratings for any lead attribute of interest. For example, when lead curvature is an attribute of interest, the lead curvature may be defined for the new and prior leads. During the lead matching function, the new and prior lead curvatures would be compared and given a similarity rating.

Once similarity ratings have been obtained for each of the select lead attributes, such as lead type, placement and orientation, for the new lead and the prior lead, flow moves to 816. At 816, the similarity ratings are combined to produce an overall lead similarity rating. By way of example, the similarity ratings for the individual lead attributes (e.g., type, placement, orientation) may be combined, using a weighted sum. For example, the lead placement $f_{lead-loc}(L_{loc,1}, L_{loc,2})$, lead type $f_{lead-type}$, and lead orientation $f_{lead-\Theta}$ each may be multiplied by a corresponding weighting value W1, W2 and W3, respectively, and the products then summed. At 816, the lead similarity rating is saved for the corresponding PETP by the APA 320 in the ratings table 327 (FIG. 3).

At 818, the process determines whether there are more pre-existing therapy profiles that have not yet been compared to the new patient profile. If more PETPs exist to be compared, flow returns to 802 where the next PETP is obtained.

Thereafter, the operations 804-816 are performed and an overall similarity rating is obtained for the next PETP. This process is repeated until the prior lead attributes of interest for all PETPs have been compared to the attributes of the new lead.

The APA 320 iteratively saves the lead similarity ratings for each of the PETPs 360 in the ratings table 327. The ratings table 327 holds a list of indices 325 to each PETP that has been analyzed as well as the corresponding lead similarity rating 323.

Optionally, the APA 320 may only save indices 325 for a select sub-set of the PETPs in the ratings table 327. For example, the APA 320 may only save indices 325 and lead similarity ratings 323 for the PETPs with lead similarity rates that exceed a predetermined lead similarity threshold. For example, the lead similarity rating may need to exceed a set number before the corresponding PETP index 325 will be saved in the ratings table 327. Alternatively, the APA 320 may maintain a running list of the top number (e.g. 10) of potential matches. Each time the process of FIG. 8 determines a similarity rating for a prior lead for a PETP, the APA 320 may determine if the lead similarity rating is in the "top N" best matches. The APA 320 may only add the PETP to the ratings table 327 if the overall similarity rating is one of the N closest matches analyzed thus far by the process of FIG. 8. In the foregoing manner, the process of FIG. 8 and comparator 322 match the pre-existing therapy profiles to the new or planned patient profile.

Next, the discussion turns to the pain and stimulation matching function ($f_{P,match}$) (the operation at 414 in FIG. 4).

Figure 10:
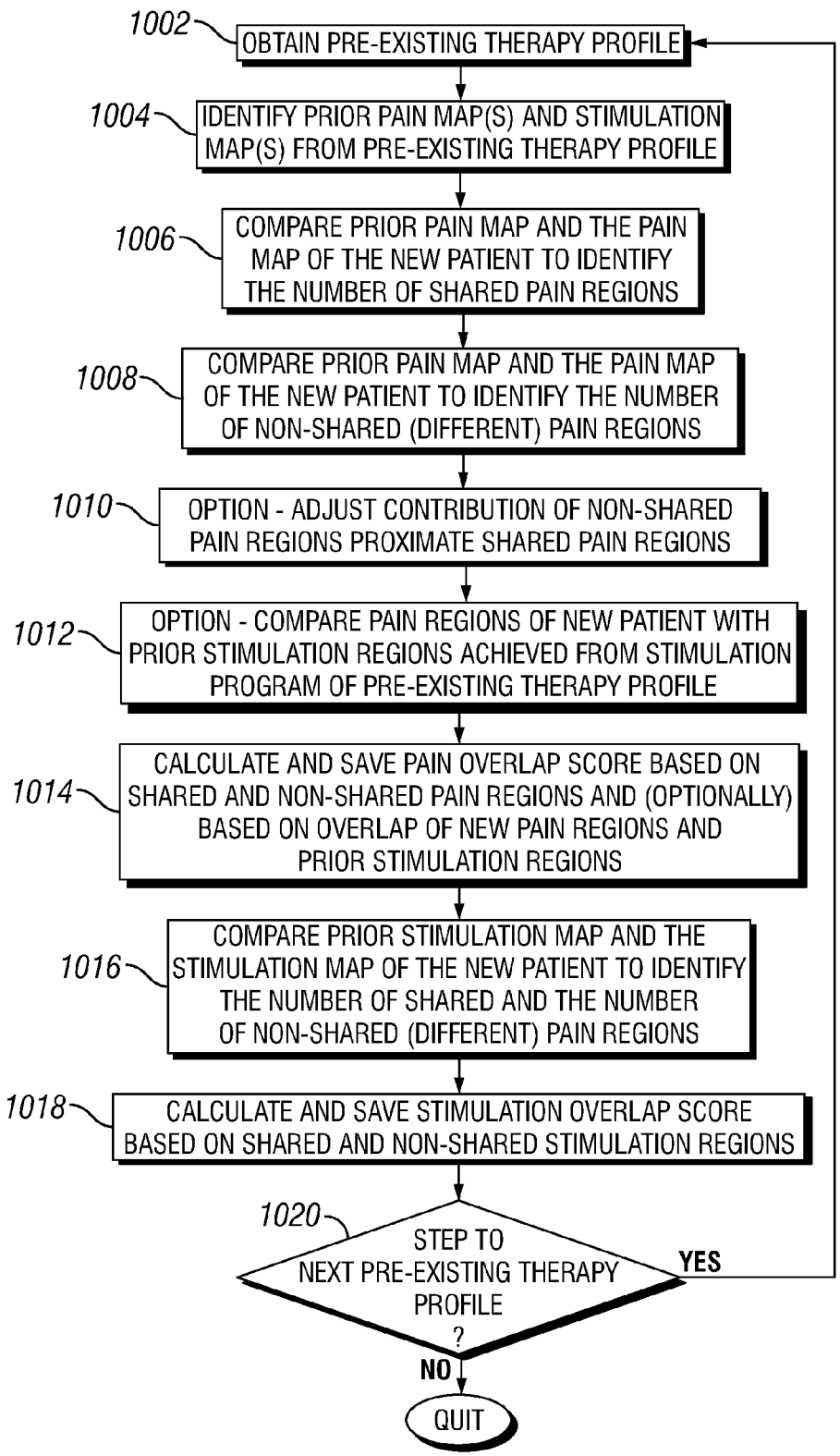
FIG. 10 illustrates a pain and stimulation matching function that may be carried out in accordance with an embodiment.

FIG. 10 illustrates the pain and stimulation matching function that may be carried out by the comparator module 322 in accordance with an embodiment. The pain and stimulation matching function is derived from a comparison of the pain and/or stimulation regions from the new pain map and from the prior pain maps of the PETPs 360. This function returns a numerical representation of the pain overlap between the new patient and prior patients.

Beginning at 1002, the next PETP 360 is obtained from storage 342. At 1004, one or more prior pain maps are identified from the PETP. As discussed above in connection with FIGS. 5 and 6, the surface area of a patient is subdivided into a number of regions ($N_{TR}$). In the example of FIG. 5, a portion of the regions (regions 61, 65 and 69) are shown to include solid hashed lines to indicate an example of a new pain map for a new patient. A portion of the regions (regions 55, 61, and 62) are shown to include dashed hashed lines to indicate an example of a prior pain map for the PETP 360.

At 1006, the process compares the prior pain map and the pain map of the new patient to identify (count) the number of shared pain regions. The count of shared pain regions ($N_{SPR}$) represents the surface area where both patients experience pain. In the example of FIG. 5, the shared pain region count $N_{SPD}$=1, namely region 61 is a pain region for the new patient and for the prior patient.

At 1008, the process compares the prior pain map and the pain map of the new patient to identify (count) the number of different or non-shared pain regions. The count of different pain regions ($N_{DPR}$) represents the surface area where the new patient experiences pain but not the prior patient, or vise versa. In the example of FIG. 5, the non-shared pain region count $N_{SPD}$=2, namely regions 65 and 69 are pain regions for the new patient, but were not pain regions for the prior patient. Also, while the prior patient experienced pain in region 55, the new patient did not experience pain in region 55.

At 1010, the process may adjust the significance of differences in the pain regions of the new and prior patients. For example, the count of different pain regions $N_{DPR}$ can be adjusted by reducing the numerical contribution or significance of differences for regions that are proximate to the pain regions that are shared by the new and prior patients. By way of example only, if there are 10 different pain regions ($N_{DPR}$=10), and 5 of these different pain regions border shared pain regions, the process may reduce the number $N_{DPR}$ by a predetermined percentage (e.g. 25%, 50%, etc.). Optionally, the operation at 1010 may be omitted entirely.

At 1012, the process may compare pain regions of the new patients with prior stimulation regions achieved from a stimulation program associated with the current PETP. If pain regions of the new patient are shared with prior stimulation regions achieved from the stimulation program of the current PETP, then the shared pain region count $N_{SPR}$ may be increased by the corresponding number of regions. For example, if the shared pain region count $N_{SPR}$ was determined at 1006 to equal 12, and at 1012, four more new pain regions were identified to match stimulation regions of the PETP, then the shared pain region count $N_{SPR}$ may be incremented by four or less. Optionally, the operation at 1012 may be omitted entirely.

At 1014, the process calculates and saves a pain overlap score $f_{P,match}(P_1,P_2)$ based on the count of shared & non-shared pain regions, as optionally modified at 1010 and 1012. For example, the counts of shared & non-shared pain regions may be combined as follows, where $P_1$ and $P_2$ represent the new and prior pain maps, and $N_{SPR}$, and $N_{DPR}$ represent counts of the shared and non-shared pain regions as discussed above:

$$f_{P,match}(P_1, P_2) = \frac{N_{SPR}}{N_{SPR} + N_{DPR}}$$

The pain overlap score for the current PETP is saved in the rating table 327. At 1016, the process compares the prior stimulation map and the stimulation map of the new patient to identify (count) the number of shared stimulation regions. The count of shared stimulation regions ($N_{SSR}$) represents the surface area where both patients experience stimulation. At 1016, the process also compares the prior stimulation map and the stimulation map of the new patient to identify (count) the number of different or non-shared stimulation regions. The count of different stimulation regions ($N_{DSR}$) represents the surface area where the new patient experiences stimulation but not the prior patient, or vise versa.

At 1018, the process calculates and saves a stimulation overlap score $f_{S,match}(S_1,S_2)$ based on the count of shared & non-shared stimulation regions, as optionally modified based on overlap of new stimulation regions and prior stimulation regions. For example, the counts of shared & non-shared pain regions may be combined in same manner as discussed above in connection with the operations at 1014. The stimulation overlap score for the current PETP is then saved in the ratings table 327. Optionally, the operations at 1016 and 1018 may be omitted entirely.

At 1020, the process determines whether there are more pre-existing therapy profiles that have not yet been compared to the new patient profile. If more PETPs exist to be compared, flow returns to 1002 where the next PETP is obtained. Thereafter, the operations of 1004-1018 are repeated and a pain overlap score and a stimulation overlap score are obtained for the next PETP. This process is repeated until the pain and stimulation information from all PETPs have been compared to the new pain and stimulation information.

The APA 320 may save the pain and stimulation overlap scores for each of the PETPs 360 in the ratings table 327. The pain overlap scores 321 and stimulation overlap scores 319 may be added to existing entries in the ratings table 327 in connecting with indices 325 to corresponding PETPs that have been analyzed. Optionally, the APA 320 may only save pain overlap scores 321 and stimulation overlap scores 319 for a select sub-set of the PETPs in the ratings table 327. For example, the APA 320 may only save pain overlap scores 321 and stimulation overlap scores 319 for the PETPs with scores that exceed predetermined pain and stimulation overlap thresholds. For example, the pain overlap scores 321 and/or stimulation overlap scores 319 may need to exceed set scores before the corresponding PETP index 325 will be saved as a potential match.

Alternatively, the APA 320 may maintain a running list of the top number (e.g., 10) potential matches. Each time the, process determines a pain overlap score and/or stimulation overlap score for a PETP, the APA 320 may determine if they are in the "top N" best matches. The APA 320 may only add the PETP to the potential candidate list when the scores are one of the N closest matches. Once pain and stimulation scores have been obtained for all of the PETPs of interest, the matching functions are complete and flow returns to the operation 416 in FIG. 4 where the list of candidate therapy profiles is created.

Returning to 416 in FIG. 4, once the matching function has been calculated between the new patient profile and every patient profile stored in the shared database, the APA 320 selects the subset of patient profiles ($S_\psi$) in the shared database for which the match function returns a profile matching score greater than or equaled to some predefined minimum score discriminator constant ($C_D$).

$$S_\Psi = \{\Psi_i, \ldots\}$$

where $$f_{match}(\psi_1, \psi_i) \geq C_D$$

At 418, for the subset of matching patient profiles ($S_\psi$), the APA 320 retrieves the set of corresponding stimulation programs ($S_\Theta$) from the storage 342 that were effective on these patients.

$$S_\Phi = \{\Phi_i, \ldots\}$$

Each stimulation program ($\Phi_i$) contains an electrode configuration and electrical stimulation parameters including amplitude, frequency, pulse width, and the like. At 418, the APA 320 constructs a recommendation (R) by removing duplicate programs from the set of matching stimulation programs and ordering the entries in order of decreasing prevalence (e.g., profiles with the most duplicates come first in the sequence). The APA 320 sends its recommendation to the programming device 304. Upon receiving this recommendation, the programming device 304 presents the recommended programs to the clinician. The clinician can test each profile manually in the order that they are presented or arbitrarily pick individual profiles from the list. The clinician may also ignore all of the recommended programs and test some other custom program.

Once an effective program (or set of programs) has been determined for the new patient, the programming device 304 sends it to the APA 320 so the stimulation program can be used to form a new PETP and be stored in the storage 342 for future consideration. Optionally, the programming device 304 can also send ineffective stimulation programs back to the APA 320 so they can be given a lower preference during future queries.

Optionally, the programming device 304 may provide various types of feedback to the APA 320 when stimulation programs are tried, abandoned or adopted. The APA 320 may then use this feedback to adjust the weights applied to lead attributes, overall lead similarity ratings, pain overlap scores and stimulation overlap scores. For example, for certain clinicians, the APA 320 may learn that the clinician places greater emphasis on similar lead attributes, not pain overlap scores. Hence, the APA 320 may increase the weight of lead similarity ratings and decrease the weight of pain overlap scores. The APA 320 may also adjust weights of individual lead attributes to increase/decrease emphasis of type, placement and/or orientation.

Optionally, systems and methods may be implemented where the lead location does not exactly match between patients by translating the recommended electrode configuration along the main longitudinal axis of the lead. This enhancement can be extended to surgical leads along the lateral axis of the lead when taking into account the electrode geometry. Further electrode mapping calculations would also allow for the inclusion of different lead types and the inclusion of differently curved leads in the recommendation.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A method to assist in programming of a neurostimulator based on a collection of pre-existing therapy profiles, the method comprising:
   obtaining a new patient profile for a new patient receiving a neurostimulator, the new therapy profile including at least one of i) a planned lead attribute, ii) a new pain map, and iii) a new stimulation map for the new patient receiving the neurostimulator;
   accessing a collection of pre-existing therapy profiles derived from prior actual patients or patient models, the pre-existing therapy profiles including stimulation programs mapped to pre-existing patient profiles, the pre-existing patient profiles having at least one of i) prior lead attribute, ii) prior pain maps, and iii) prior stimulation maps for prior patients or models of patients;
   comparing the new patient profile with at least a portion of the collection of pre-existing patient profiles to generate profile matching scores indicating an amount of similarity between the pre-existing patient and the new therapy profile; and
   producing a list of candidate therapy profiles that includes at least one potential stimulation program that is mapped to at least one pre-existing patient profile having a profile matching score that satisfied a match threshold.

2. The method of claim 1, wherein the accessing includes querying at least one database that stores the collection of pre-existing therapy profiles.

3. The method of claim 1, wherein the obtaining includes:
   displaying a virtual lead and a graphical representation of an anatomy of interest, and
   permitting a clinician to at least one of position and orient the virtual lead on the anatomy of interest at a corresponding placement or orientation representative of a position or an orientation at which an actual lead was implanted in the new patient.

4. The method of claim 1, wherein the anatomy of interest includes a virtual representation of a series of vertebra locations, the method permitting the clinician to locate electrodes of the virtual lead at desired angular orientations with respect to a reference axis on a select vertebra location.

5. The method of claim 3, further comprising displaying at least one of position and orientation markers relative to the graphical representation, the markers subdividing the anatomical structure into multiple sections, the clinician at least one of positioning and orienting the virtual lead relative to the position markers.

6. The method of claim 1, wherein the obtaining includes:
displaying at least one of position and orientation markers; and
permitting a clinician to enter the planned lead attribute relative to the markers.

7. The method of claim 1, wherein the planned and prior lead attributes include at least one of lead type, lead placement and lead orientation.

8. The method of claim 1, wherein the obtaining includes recording, as the planned lead attribute, at least one of a new lead type, new lead placement and new lead orientation after implantation of the lead relative to anatomical structure in a manner that is independent of variations in patient dimensions.

9. The method of claim 1, wherein the comparing includes utilizing a matching function to generate similarity ratings between the planned and prior lead attributes of the new patient profile and the pre-existing patient profiles, and utilizing the similarity ratings to generate the profile matching scores.

10. The method of claim 9, wherein the matching function forms the similarity ratings between at least one of i) a planned lead placement and prior lead placements and ii) a planned lead orientation and prior lead orientations.

11. The method of claim 1, wherein the comparing includes utilizing a matching function to form pain overlap scores between the new pain map and the prior pain maps, and utilizing the pain overlap scores to generate the profile matching scores.

12. A system to assist in programming a neurostimulator based on a collection of pre-existing therapy profiles, the system comprising:
an input device to obtain a new patient profile for a new patient receiving a neurostimulator, the new therapy profile including at least one of i) a planned lead attribute, ii) a new pain map, and iii) a new stimulation map for the new patient receiving the neurostimulator;
a storage storing a collection of pre-existing therapy profiles derived from prior actual patients or patient models, the pre-existing therapy profiles including stimulation programs mapped to pre-existing patient profiles, the pre-existing patient profiles having at least one of i) prior lead attributes, ii) prior pain maps, and iii) prior stimulation maps for prior patients or models of patients;
a comparator module to compare the new patient profile with at least a portion of the collection of pre-existing patient profiles to generate profile matching scores indicating an amount of similarity between the pre-existing patient profiles and the new therapy profile; and
a candidate module to produce a list of candidate therapy profiles that includes at least one potential stimulation program that is mapped to at least one pre-existing patient profile having a profile matching score that satisfied a match threshold.

13. The system of claim 12, wherein the storage includes a database that stores the collection of pre-existing therapy profiles.

14. The system of claim 12, wherein the input device includes:
a display to display a virtual lead and a graphical representation of an anatomy of interest, and
a user interface to permit a clinician to at least one of position and orient the virtual lead on the anatomy of interest at a position or orientation representative of a planned vertebra location at which an actual lead was implanted in the new patient.

15. The system of claim 14, wherein the display displays, as the anatomy of interest, a virtual representation of a series of vertebra, the user interface to permit the clinician to locate electrodes of a virtual lead at a desired horizontal, vertical or orientation alignments on the planned vertebra location.

16. The system of claim 12, wherein the input device includes:
a display to display at least one of position and orientation markers relative to a graphical representation of an anatomy of interest, the markers subdividing the anatomy of interest into multiple sections; and
a user interface to permit a clinician to enter the planned lead attribute relative to the markers to designate at least one of position and orientation at which an actual lead was implanted in the new patient.

17. The system of claim 16, wherein the display displays, on the patient anatomy of interest, the markers in a non-linear scaled manner proportioned to a size of the anatomy of interest, thereby decoupling lead placement from a size of the anatomy of interest.

18. The system of claim 12, wherein the input device records at least one of the new lead type and new lead placement after implantation of the lead relative to anatomical structure in a manner that is independent of variations in patient dimensions.

19. The system of claim 12, wherein the comparator module utilizes a matching function to generate similarity ratings between the planned and prior lead attributes of the new patient profile and the pre-existing patient profiles, and utilizing the similarity ratings to generate the profile matching scores.

20. The system of claim 19, wherein the matching function forms similarity ratings between at least one of i) a planned lead placement and prior lead placements, and ii) a planned lead orientation and prior lead orientation, the candidate module utilizing the similarity ratings to product the list of candidate therapy profiles.

21. The system of claim 12, wherein the comparator module utilizes a matching function to form pain overlap scores between the new pain map and the prior pain maps, the candidate module utilizing the pain overlap scores to produce the list of candidate therapy profiles.

22. The system of claim 12, wherein the planned and prior lead attributes include at least one of lead type, lead placement and lead orientation.

* * * * *